United States Patent [19]

Gewain et al.

[11] Patent Number: 5,252,474
[45] Date of Patent: Oct. 12, 1993

[54] CLONING GENES FROM STREPTOMYCES AVERMITILIS FOR AVERMECTIN BIOSYNTHESIS AND THE METHODS FOR THEIR USE

[75] Inventors: Keith M. Gewain, Middelsex; Douglas J. MacNeil; Tanya MacNeil, both of Westfield; Philip S. paress, Maplewood; Carolyn L. Ruby, Montclair; Stanley L. Streicher, Verona, all of N.J.

[73] Assignee: Merck & Co., Inc., Rahway, N.J.

[21] Appl. No.: 490,723

[22] Filed: Mar. 14, 1990

Related U.S. Application Data

[63] Continuation-in-part of Ser. No. 390,576, Aug. 7, 1989, abandoned, which is a continuation-in-part of Ser. No. 331,146, Mar. 31, 1989, abandoned.

[51] Int. Cl.$^5$ .................... C12N 15/00; C12N 15/11; C12P 17/18
[52] U.S. Cl. .................... 435/172.3; 435/119; 435/252.33; 435/252.35; 435/320.1; 435/76; 935/9; 935/29; 935/72; 935/73; 935/75
[58] Field of Search .................... 435/71.2, 71.3, 320.1, 435/172.3, 252.3, 76, 252.33, 119, 252.35, 886; 935/9, 29, 72, 73, 75; 536/27

[56] References Cited

U.S. PATENT DOCUMENTS 4,703,009  10/1987  MacNeil et al. .................. 435/172.3

FOREIGN PATENT DOCUMENTS 118367  9/1984  European Pat. Off. .
173327  3/1986  European Pat. Off. .
204549  12/1986  European Pat. Off. .
276103  7/1988  European Pat. Off. .
276131  7/1988  European Pat. Off. .
62-195286  2/1986  Japan .
62-224292  3/1986  Japan .
8703907  7/1987  World Int. Prop. O. .

OTHER PUBLICATIONS

The Extended Phenotype, 1982, Dawkins, Oxford University Press, Oxford, pp. 85, 86, and 287.
Hutchinson; Applied Biochemistry and Biotechnology 16: 169 (1987).
Murooka et al; Agric. Biol. Chem. 47: 1807 (1983).
Hopwood, et al Nature 314, pp. 642-644.
Schulman, et al, Jour. of Antib. 38 pp. 1494-1498 (1985).
Ruby, et al Sixth Annual Symposium on Actinomycetes Bio. pp. 279-280 (1985).
Ikeda, et al J. Bacteriol. 169, pp. 5615-5621 (1987).
Chater, et al EMBO Jour. 4, pp. 1893-1897 (1985).
Malpartida, et al Nature 309 pp. 462-464 (1984).
Schulman, et al Antimicrobial Agents and Chemotherapy 31 pp. 744 and 746 only (1987).
Fishman, et al Proc. Natl. Acad. Sci. USA 84 pp. 8248-8252 (1987).
Motamedi, et al Proc. Natl. Acad. Sci. USA 84 pp. 4445-4449 (1987).
McNeil, J. Microbiol. Methods 5 pp. 115-123 (1986).
Feitelson, et al J. Gen. Microbiol. 131 pp. 2431-2441 (1985).
Murakami, et al Mol. Gen. Genet. 205 pp. 42-50 (1986).
MacNeil, et al J. Industrial Microbiol. 2 pp. 209-218 (1987).
Chen, et al Bio/Technology 6 pp. 1222-1224 (1988).
Miller, et al Antimicrobial Agents and Chemotherapy 15 pp. 368-371 (1979).
Ruby et al, "Isolation and Characterization of Streptomyces Aremitilis Mutants Defective in the Methylation of the Avermectins"—Conference Paper (1980)—Abstract only.

*Primary Examiner*—James Martinell
*Attorney, Agent, or Firm*—David L. Rose; Joseph F. DiPrima

[57] ABSTRACT

There are disclosed plasmids containing DNA isolated from *Streptomyces avermitilis*, the microorganism which is used to prepare avermectin compounds, identified as pAT1, pVE650 pVE855, pVE859, pVE1446, pVE923, and pVE924 which contain the genetic information for the biosynthesis of the avermectins. Methods for the isolation of such plasmid and for the manipulation of the plasmids to alter the formation of the avermectin compound are also disclosed.

46 Claims, 7 Drawing Sheets

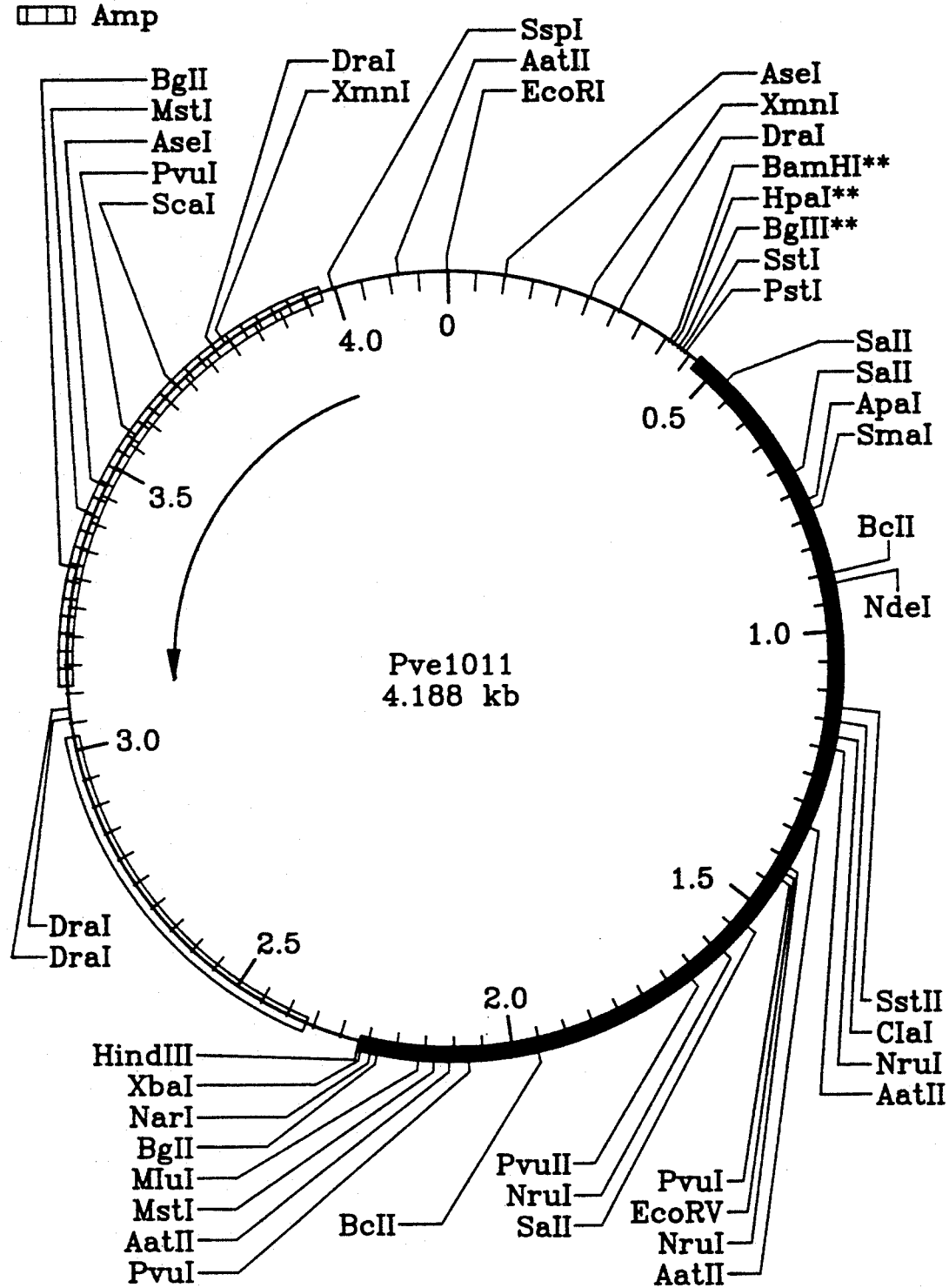

CLONING GENES FROM STREPTOMYCES AVERMITILIS FOR AVERMECTIN BIOSYNTHESIS AND THE METHODS FOR THEIR USE

CROSS REFERENCE TO RELATED APPLICATIONS

This case is a continuation-in-part of our application Ser. No. 390,576 filed Aug. 7, 1989, now abandoned, which in turn is a continuation-in-part of application Ser. No. 331,146, filed Mar. 31, 1989 now abandoned.

BACKGROUND OF THE INVENTION

Streptomyces are producers of a wide variety of secondary metabolites, including most of the commercial antibiotics. Because of this, considerable effort has been invested in developing gene cloning techniques for Streptomyces. Procedures for the efficient introduction of DNA into Streptomyces by polyethylene glycol (PEG) mediated transformation have been developed. Vectors have been constructed which include phages, high copy number plasmids, low copy number plasmids and *E. coli*-Streptomyces shuttle vectors. Numerous drug resistance genes have been cloned from Streptomyces species and several of these resistance genes have been incorporated into vectors as selectable markers. A review of current vectors for use in Streptomyces is Hutchinson, *Applied Biochemistry and Biotechnology* 16 pg 169-190 (1988). In many cases, genes for the production of secondary metabolites and genes encoding for resistance have been found to be clustered. Thus one strategy for cloning genes in a pathway has been to isolate a drug-resistance gene and then test the adjacent DNA for other genes for that particular antibiotic. Examples of biosynthetic genes clustered near a drug resistance gene include actinorhodin (Malpartida and Hopwood, *Nature* 309 pg 462 (1984)), tetracenomycin C (Motamedi and Hutchinson, *Proc. Natl. Acad. Sci. USA* 84 pg 4445-4449 (1987)), and bialaphos (Murakami et al, *Mol. Gen. Genet.* 205 p 42-50 (1986), EP 173,327). EP 204,549 exploits the clustering of drug-resistance genes and biosynthetic genes and claims a method for isolating antibiotic genes by using a easily isolated drug-resistance gene. Patent publication wo87/03907 discloses a method for isolating polyketide antibiotics using cloned genes for polyketide synthase. This application also discloses the cloning of genes involved in milbemycin biosynthesis, a compound structurally related to the avermectins. Another strategy for cloning genes for the biosynthesis of commercially important compounds has been complementation of mutants. A library of DNA from a producing organism is introduced into a nonproducing mutant and the transformants are screened for the production of the compound. This approach has also identified gene clusters involved in antibiotic production, in some cases all the genes for the production of several antibiotics have been cloned. In addition to the three examples above, other examples of cloned Streptomyces genes involved in antibiotic biosynthesis include tylosin (Fishman et. al., *Proc. Natl. Acad. Sci. USA*, 84 pg 8248-8252 (1987), undecylprodigiosin (Feitelson, et al., *J. Gen. Micro.* 131 pg 2431-2441 (1985), methylenomycin (Chater and Bruton, *EMBO J* 4 pg 1893-1897 (1985), nosiheptide (JP 8636216) and Cephamycin C (Chen et al., *Bio/Technology* 6 pg 1222-1224 (1988), JP 8667043). In several cases new analogs of antibiotics have been produced by the introduction of cloned genes into other Streptomyces (Floss, *Biotechnology* 5 pg 111-115 (1987), Hopwood et al., *Nature* 314 pg 642-644 (1985)). In other cases the introduction of extra copies of biosynthetic genes into the original producing organism has resulted in increased titer of the antibiotic. EP 238323 discloses the process of introducing a gene for the rate limiting enzyme into the producing organism to increase titer of the antibiotic.

*Streptomyces avermitilis* produces avermectins, a series of 8 related compounds with potent anthelmintic and insecticidal activity (U.S. Pat. Nos. 4,310,519 and 4,429,042). A semisynthetic derivative of avermectin, ivermectin, is a commercially important anthelmintic. U.S. Pat. No. 4,310,519 describes a mutant of *S. avermitilis* which lacks the furan ring of the natural avermectins. Schulman et al., *J. antibiot.* 38 pg 1494-1498 (1985) describes a mutant, Agly-1, which produces avermectin aglycones A1a and A2a. Ruby et al., *Proceedings of the 6th International Symposium on the Biology of Actinomycetes*, G. Szabo, S. Biro, M. Goodfellow (eds.), p.279-280 (1985) and Schulman et al., *Antimicr. Agents and Chemother.* 31 pg 744-747 (1987) describe 2 classes of *S. avermitilis* mutants, one class is defective in O-methylation at C-5 and the other class is defective in O-methylation at C-3" and C-3'. EP 276103 describes a mutant of *S. avermitilis* defective in branch chain fatty acid dehydrogenase. EP 276131 describes a *S. avermitilis* mutant defective in C-5, C-3", and C-3' O-methylation. Ikeda et al., *J. Bacteriol.* 169 pg 5615-5621 (1987), have described the isolation and genetic analysis of two classes of *S. avermitilis* mutants. AveA mutants were defective in avermectin aglycone formation and AveB mutants failed to synthesize or attach the oleandrose moiety to avermectin aglycone. They obtained genetic evidence that the two classes of mutations are linked. This application describes the cloning of genes required for the biosynthesis of avermectins. Other microorganisms that produce avermectin-like-compounds are *S. hygroscopicus, S. cyanogrieseus* and *S. thermoarchaenosis*. Such microorganisms may be subjected to the same procedures as are described herein for *S. avermitilis*.

SUMMARY OF THE INVENTION

Mutants of *S. avermitilis* which produce analogs of the 8 major avermectins, mutants which produce avermectins in a different ratio than the original soil isolate, and mutants which fail to produce avermectins, were isolated from mutagenized cells. A gene library of *S. avermitilis* DNA was made in the low copy number Streptomyces vector pIJ922. After ligation, the resulting molecules were transformed into *S. lividans* and transformants were selected as thiostrepton resistant (Thio'). Transformants were pooled and plasmid DNA was isolated. Aliquots of the pIJ922 library were introduced into mutants of *S. avermitilis*. Several plasmids were discovered which complemented the defect in an avermectin C-5 O-methyltransferase (OMT) deficient strain. The first plasmid, pAT1, was characterized extensively. Another plasmid, pVE650, was discovered which complemented the defect in an avermectin aglycone producing mutant, this mutant is defective in synthesis or addition of oleandrose moiety to the avermectin aglycone. Subcloning analysis of pAT1 revealed the gene for OMT was located on a 3.4 kb BamHI fragment. Subcloning analysis of pVE650 revealed that two BglII fragments complemented the defect in several avermectin aglycone producing strains.

Southern hybridization analysis of pAT1 and pVE650 indicated that the two plasmids do not contain any overlapping sequences. However, it was surprisingly discovered that the two plasmids contain regions of non-exact, but related homology. Two different groups of related sequences were discovered. The number of different BamHI fragments from the genome of *S. avermitilis* that are in each group was determined by a Southern analysis of the BamHI digested *S. avermitilis* genomic DNA. Seven separate BamHI fragments showed homology to a probe from Group 1. These 7 were composed of 1 fragment located on the DNA cloned on pAT1, one fragment on the DNA cloned on pVE650, and 5 other bands located elsewhere in the chromosome. At least 14 BamHI fragments contained regions of homology to a probe from Group 2. Five fragments of pVE650, 1 fragment of pAT1, and 8 fragments elsewhere in the genome of *S. avermitilis* contained regions homologous to a Group 2 probe.

A second gene library of *S. avermitilis* DNA was made in the *E. coli* cosmid vector pVE328. Restriction fragments from pVE650 were used as probes to isolate clones from the pVE328 cosmid library that contained sequences homologous to pVE650. A series of cosmid clones were isolated that collectively span over 110 kb of genomic DNA. This DNA includes the avermectin C-5 O-methylransferase gene, the C-22, C-23 dehydrase gene, several genes involved in avermectin aglycone formation, and at least 7 genes involved in the synthesis or attachment of oleandrose to avermectin aglycone.

One region of the avermectin gene cluster was missing from the cosmids that were isolated. This region was cloned directly from the *S. avermitilis* genome into *E. coli* using an integration vector. An additional 15 kb of the avermectin gene cluster was cloned this way.

DETAILED DESCRIPTION OF THE INVENTION AND ITS PREFERRED EMBODIMENTS

ISOLATION AND CHARACTERIZATION OF AVERMECTIN MUTANTS

Mutants defective in avermectin biosynthesis were detected by a thin layer chromatography (TLC) screen of methanol extracts derived from fermentations of single colony survivors of mutagenic treatments. Spores of the parental strains were mutagenized with UV or NTG as described in Hopwood et al., *Genetic manipulations of Streptomyces-A Laboratory manual*, John Innes Institute. Norwich. 1985. The survivors of the treatment, which killed 99% to 99.9% of the spores, were allowed to form well sporulated colonies on Medium A. Spores from a single colony were inoculated into 0.25 ml of growth medium. After 40 hours of growth, 0.8 ml of fermentation medium was added and the fermentation continued for 13 days. Fermentations were incubated at 28° C. on a rotary shaker at 220 rpm. Various growth media and fermentation media can be used, several media have been described in U.S. Pat. Nos. 4,310,519 and 4,378,353. A growth medium which is particularly useful is Medium B, and a fermentation medium which is particularly useful is Medium C.

| Medium A | |
|---|---|
| $KNO_3$ | 1 g |
| Yeast Extract (Difco) | 1 g |
| Malt Extract | 1 g |
| Sodium Citrate | 0.5 g |
| $MgSO_4.7H_2O$ | 0.25 g |
| Trace Elements | 2.5 ml |
| Glucose | 2 g |
| Distilled water | 1000 ml |
| Adjust to pH 7.0 with NaOH | |
| Trace elements for Medium A contain per liter of distilled water: 49.7 ml HCl (37.3%), 61.1 g $MgSO_47H_2O$, 2.0 g $CaCO_3$, 5.4 g $FeCl_3.6H_2O$, 1.44 g $ZnSO_4.7H_2O$, 1.11 g $MnSO_4H_2O$, 0.25 g $CuSO_45H_2O$, 0.062 g $H_3BO_3$, and 0.49 g $Na_2MoO_4.H_2O$. | |
| Medium B | |
| $MgSO_4.7H_2O$ (12.5% solution) | 2.67 ml |
| NaCl (12.5% solution) | 2.67 ml |
| $MnSO_4.H_2O$ (0.5% solution) | 0.67 ml |
| $ZnSO_4.7H_2O$ (1.0% solution) | 0.67 ml |
| $CaCl_2.H_2O$ (2.0% solution) | 0.67 ml |
| $FeSO_4.7H_2O$ (2.5% solution) | 0.67 ml |
| $KNO_3$ | 1.33 g |
| Hy-Case S.F. (Humpko) | 13.3 g |
| Yeast Extract (DIFCO) | 13.3 g |
| Glucose | 19.95 g |
| Distilled Water | 1000 ml |
| Adjust pH to 7.0 with 1N NaOH | |
| Medium C | |
| Peptonized Milk | 20 g |
| Ardamine pH | 4 g |
| Glucose | 105 g |
| $MgSO_4.7H_2O$ | 0.5 g |
| $CuSO_4.5H_2O$ | 0.06 g |
| $ZnSO_4.6H_2O$ | 1 mg |
| $CoCl_2.6H_2O$ | 0.1 mg |
| $FeCl_2.6H_2O$ | 3 mg |
| Add Distilled water to a volume of | 900 ml |
| Adjust to pH 7.2 w/1 N NaOH | |

Separately prepare a glucose solution of 35 g of glucose in a final volume of 100 ml of distilled water, adjust pH to 7.2. After autoclaving add the glucose solution to complete Medium C.

The fermentation broth was extracted with an equal volume of methanol and a sample was applied to a TLC plate to separate the avermectins. The TLC system employed separates the avermectins into 4 bands detected by UV fluorescence quenching as described by Miller et al., *Antimicrob. Agents and Chemother.* 15, 368–371, (1979). Extracts were spotted on E. Merck Silica Gel 60 F-254 plates and developed in a solvent of Dichloromethane: Ethyl Acetate: Methanol 9:9:1. In this system, the order of the avermectins from fastest to slowest band is avermectin A1, A2, B1, and B2; the a and b series are not resolved. Colonies showing compositional changes, bands of altered mobility, or the absence of some or all avermectin bands were repurified and refermented. Mutants which were stable and gave reproducible fermentations were saved. The avermectins produced by some of the mutants were isolated by preparative TLC and HPLC and characterized by NMR or mass spectroscopy when necessary for identification. In most cases identification was established through direct comparison with pure samples of individual components (e.g. Bla for identifying mutants deficient in O-methyltransferase activity) or modified avermectins (e.g. avermectin aglycones or, desmethylavermectins) obtained through chemical modification or fermentations in the presence of inhibitors (Schulman et al., *J. Antibiot.* 38 1494–1498 (1985)). Table 1 presents a summary of the mutant classes isolated.

TABLE 1

Avermectin Mutants of *Streptomyces avermitilis*

| Mutant Class | Fermentation Products |
| --- | --- |
| Non-producers | None |
| Aglycone producers (AGL)[1] | Avermectin aglycones |
| Oleandrose synthesis | |
| TDP-Oleandrose tranferase(s) | |
| Avermectin C5—O-methyl-transferase (OMT)[1] | Avermectin B1(a + b) + B2(a + b) |
| TDP-demethyloleandrose 3-O-methyl-transferase (GMT)[1] | 3′, 3″ Demethyl avermectins |
| Dehydrase | Avermectins A2(a + b) + B2(a + b) |
| Furan ring | Defurano avermectins |

[1]AGL: aglycone producer; OMT: O-methyltransferase; GMT: glycosyl O-methyltransferase The classified mutants were those where the blocks occurred after the formation and closure of the macrolide ring structure, since detectable fermentation products accumulated which could be isolated and identified. These include two types of O-methyltransferase mutants. The first class is defective in methylation at the C-5 position (avermectin O-methyltransferase) and results in the accumulation of avermectin B components (OMT⁻ phenotype) Ruby et al., *Proceedings of the 6th International Symposium on the Biology of Actinomycetes*, G. Szabo, S. Biro, M. Goodfellow (eds.), p. 279-280 (1985) and (Schulman et al., *Antimicr. agents and Chemother.* 31 pg 744-747 (1987)). The second class is deficient in methylation of the oleandrose moieties (glycosyl O-methyltransferase) resulting in the accumulation of desmethylavermectins (GMT⁻ phenotype) Ruby et al., *Proceedings of the 6th International Symposium on the Biology of Actinomycetes*, G. Szabo, S. Biro, M. Goodfellow (eds.), p. 279-280 (1985) and (Schulman et al., *Antimicr. agents and Chemother.* 31 pg 744-747 (1987)). Biochemical studies have indicated that these methylation reactions are catalyzed by at least two distinct enzymes. A large class of avermectin mutants are unable to synthesize or attach the oleandrose moiety to avermectin aglycones. These mutants accumulate the avermectin aglycones and are defective in either the synthesis of oleandrose diphosphonucleotide or the transfer of its oleandrose moiety. Other characterized mutants include those unable to close the furan ring and those with reduced ability to catalyze the conversion of avermectin "2" precursors to avermectin "1" precursors. The latter mutants accumulate primarily the avermectin "2" components and are presumed to lack "avermectin" dehydrase activity.

The class of avermectin non-producing mutants presumably represents many different blocks in the early steps of avermectin synthesis. These mutants may be producing enzyme bound intermediates but do not appear to accumulate any diffusable intermediates or U.V. absorbing material capable of being transformed into avermectins. Pair-wise fermentations of these non-producing mutants did not lead to the production of avermectins. Methanol extracts of non-producers did not contain precursors able to be converted into avermectins. Thus the avermectin non-producers have not yet been classified into different groups.

Mutants unable to methylate avermectin at the C-5 hydroxy position produce avermectins B1 (a+b) and B2 (a+b) almost exclusively. These mutants have low or undetectable levels of avermectin OMT, an enzyme which utilizes S-adenosylmethionine as the methyl donor (Schulman et al., *Antibiot*. 38 1494-1498 (1985). The levels of A components found in some mutants are related to the leakiness of the defect since low but detectable amounts of enzyme were also found to be present. The mutant phenotype appears to be closely correlated to the lack of the OMT enzyme. Since the overall avermectin titer of these mutants is unchanged from that of the parental strain, it is likely that mutations responsible for the OMT phenotype are structural gene lesions. Among the avermectin mutants isolated, the OMT class is the best characterized and understood. This class was used first in the complementation screen.

CLONING THE GENE FOR C-5 AVERMECTIN O-METHYLTRANSFEREASE

A genomic library in the low copy-number Streptomyces vector pIJ922 (Hopwood et al., *Genetic Manipulations of Streptomyces a Laboratory Manual*, John Innes Institute, Norwich, 1985) was used for the mutant complementation screen. The library was constructed by ligating *S. avermitilis* DNA, which had been partially digested with Sau3A and size fractionated, into pIJ922, which had been linearized with BamHI restriction enzyme and treated with calf intestinal alkaline phosphatase. The ligated DNAs were then transformed into either *S. lividans* or *S. avermitilis* and thiostrepton resistant colonies were selected. Sporulated colonies were harvested in bulk, diluted into YEME medium (Hopwood et al., *Genetic Manipulations of Streptomyces a Laboratory Manual*, John Innes Institute, Norwich, 1985) and cultured for plasmid purification. The purified plasmid preparations from these cultures constitute the pIJ922-*S. avermitilis* genomic library. A representative number of initially transformed colonies and those derived from a transformation using the purified library plasmid preparations were checked for insert frequency and size. The frequency of plasmids containing inserts was greater than 65% with an average size of about 20 kb. Neither the frequency nor that average insert size differed significantly between the initial set of transformants and that obtained with library DNA.

The library was initially screened by transforming avermectin O-methyltransferase deficient (OMT⁻) mutant, MA6233, with library DNA selecting for Thio$^r$ transformants. Individual transformed colonies were scored for avermectin production and composition. The OMT mutant produces only two avermectin TLC bands under these conditions (B1 and B2). One OMT positive transformant was detected from screening over 10,000 transformants. This transformant was purified, retested for complementation and the plasmid from one of the repurified colonies was designated pAT1. Plasmid pAT1 complemented the OMT phenotype of all 6 OMT mutants tested. A restriction map of pAT1, which contains 20 kb of *S. avermitilis* DNA, was determined. The location of sites is presented in Table 3 and the map is indicated in FIG. 1. The gene for O-methyltransferase was designated avrA. Plasmid pAT1 was transformed into *S. lividans*, and the resulting strain designated MA6619 which has been deposited as ATCC 67820 at the American Type Culture. Collection, 12301 Parklawn Dr., Rockville, Md. 20852.

The OMT gene was localized by subcloning pAT1 BamHI fragments into pIJ922, followed by transformation and complementation analysis. A subclone pAT83 containing the 3.4 kb BamHI fragment, was able to complement MA6233 ($OMT^-$), indicating that the gene maps within this fragment.

CLONING GENES OF OLEANDROSE SYNTHESIS AND/OR TRANSFER

Subsequent to the isolation of the pAT1 an additional screening effort was undertaken to isolate plasmids that would complement other avermectin mutants. Aliquots of the pIJ922 library were transformed into MA6278 ($AGL^-$, $OMT^-$). Transformants were screened for the production of glycosylated avermectins. This effort led to the isolation of pVE650, a plasmid containing an insert of about 24 kb that complements a number of mutant strains defective either in the synthesis of oleandrose or its transfer to avermectin aglycone. Table 2 shows that pVE650 complemented the defect in 21 aglycone producing mutants but five aglycone producing mutants were not complemented indicating that some glycosylation genes are outside of this cloned region. Neither pVE650 nor pAT1 complemented an avermectin non-producing mutant or a $GMT^-$ mutant. A restriction map was established for the pVE650 insert (FIG. 2) and Table 4 presents the location of the restriction sites. A comparison with the map of pAT1 does not indicate any fragment in common between the two clones. This plasmid was introduced into *S. lividans* and the resulting strain designated MA6618. This strain has been deposited as ATCC 67819.

Complementation analysis of pVE650.

Three avermectin genes involved in oleandrose synthesis or attachment have been identified by complementation studies with pVE650, and two subclones. pVE650 is a plasmid with a 24 kb insert of *S. avermitilis* DNA which contains genes for the synthesis and/or addition of oleandrose to the avermectin aglycone. A subclone, pVE806, which is pIJ922 with the 4.28 kb BglII fragment cloned into the BamHI site, was found to complement some aglycone producing mutants (Class I in Table 2). Another subclone, pVE807, composed of the 2.56 kb BglII fragment inserted into the BamHI site of pIJ922, complemented other mutants (Class II). Class III consists of the mutants which are complemented by PVE650 but not by any subclones tested. It is quite possible that each class may include more than one gene.

TABLE 2

| | | Complementation of *S. avermitilis* avermectin aglycone producing mutants | | | | | | |
|---|---|---|---|---|---|---|---|---|
| Class | Mutants | pVE650[1] | pVE908 | pVE807 | pVE941 | pVE1018 | pVE1420 | pVE1116 |
| I | GG900, MA6595, MA6586, MA6593, MA6056, MA6624 | + | + | − | − | − | − | + |
| II | MA6582, GG898, MA6579, MA6581, MA6589, MA6591, MA5872 | + | − | + | + | − | − | + |
| III | MA6278, MA6580, MA6583, MA6584, MA6585, MA6587, MA6588, MA6060 | + | − | − | + | − | − | + |
| IV | MA6057, MA6622, | − | − | − | + | − | − | + |
| V | MA6590 | − | − | − | + | − | + | + |
| VI | MA6592, MA6594 | − | − | − | + | + | + | + |
| GMT | MA6316, MA6323 | − | − | − | + | − | + | + |

[1]The indicated plasmid was transformed into the mutants and at least 6 transformants were tested for avermectin production. The vector alone, pIJ922, was indtroduced into the mutants and assayed as a negative control.

Class I mutants have been tested by other subclones of pVE650. One other subclone which complemented the mutants of Class I was the 4.05 kb EcoRI fragment when cloned onto pIJ922 in one orientation (pVE808). However when cloned in the other orientation (pVE818) a partially complemented or mixed TLC pattern is observed which includes both aglycones and glycosylated forms of avermectin. This may be the result of recombination correcting the defect rather than complementation. Alternatively, the gene which complements the defect in the Class I mutants may be poorly expressed from pVE818 and there may be insufficient amounts of the protein necessary to produce fully glycosylated avermectins. If this is so, it may indicate that the promoter for these genes is located between the BglII site at 17.75 kb and EcoRI site at 19.67 kb on the pVE650 map. When the 2.36 kb EcoRI-BglII fragment is cloned onto pIJ922, resulting in pIJ908, the Class I mutants were also complemented, indicating that all the information to correct the defects in these mutants is located within this fragment. The gene represented by Class I is designated avrC.

Class II mutants are corrected by pVE807 which is pIJ922 with the 2.56 kb BglII fragment. The gene represented by Class II mutants is designated avrD.

Class III mutants are only complemented by pVE650. No complementation was seen with either pVE808, pVE806, pVE807 or pVE845. pVE845 is a derivative of pIJ922 with the 19.67 kb EcoRI fragment of pVE650 (FIG. 2) inserted in the EcoRI site. pVE845, pVE806, pVE807, and pVE808 contain all the sequences on pVE650. Since none of these clones complements Class III mutants, the gene or operon represented by Class III mutants must span the region of overlap by these plasmids. The gene represented by Class III mutants is designated avrB.

Five aglycone producing mutants are not complemented by pVE650. Since a cluster of at least 3 genes for oleandrose synthesis or addition was located on pVE650, and this cluster was mapped to one end of the insert DNA of pVE650, it was possible that the other gene(s) for oleandrose synthesis or attachment were chromosomally located adjacent to the insert on pVE650. As described below, cosmid clones containing this region were isolated and a BglII fragment was identified which includes the region of pVE650 beginning at the BglII site at 22.03 kb on the pVE650 map and extending about an additional 14 kb. This BglII fragment was subcloned onto pIJ922 to yield plasmid pVE941. This plasmid was found to complement the aglycone producing mutants not complemented by pVE650. In addition, pVE941 complemented GMT− strain, MA6316, indicating that the gene for TDP-demethyl-oleandrose 3-O-methyltransferase, designated avrF, is also on this fragment.

Southern hybridization analysis of pVE650 restriction fragments and genomic DNA suggests that the insert DNA in pVE650 is colinear with the chromosome and that there are two groups of reiterated or related sequences within the insert. Probes made from three of the 10 BamHI fragments of pVE650 (the 2.22 kb, 1.09 kb, and 0.53 kb BamHI fragments) hybridize with only a single fragment either in the chromosome or in pVE650. Group 1 consists of 1 BamHI fragment in pVE650 (2.09 kb), 1 fragment in pAT1 (0.55 kb BamHI), and 5 other chromosomal fragments. Probes made from BamHI fragments in a second group of related sequences, Group 2, hybridize with themselves as well as 4 other BamHI fragments within pVE650 (the 7.0 kb, 4.6 kb, 3.0 kb, 1.82 kb, and 1.38 kb BamHI fragments) and 9 other chromosomal BamHI fragments including one BamHI fragment in pAT1 (the 2.1 kb BamHI fragment). The degree of homology, as indicated by the relative intensity of hybridizing bands, varied significantly depending upon which of the cloned fragments within each group was the probe suggesting inexact sequence homology among these related sequences.

Isolation of cosmids containing a 110 kb avermectin gene cluster

As described above, 5 aglycone producing mutants are not complemented by pVE650. Since the complementing region of pVE650 was located to one end of the clone, it was possible that other avermectin genes are located on the adjacent chromosomal DNA. The 1.09 kb BamHI fragment of pVE650 (Table 4) was used to probe a cosmid library of S. avermitilis DNA. DNA from 7 of these clones which overlapped the 1.09 kb BamHI fragment were mapped with respect to the different BamHI fragments of pVE650. One cosmid, pVE855, contains all of the DNA on pVE650 and adjacent DNA on both sides. Another cosmid, pVE859, extends at least 26 kb past the region of pVE650 that complements the aglycone mutants (away from avrA the gene for avermectin O-methyltransferase). At least 31 kb of DNA adjacent to pVE650 was cloned.

Since genes for antibiotic synthesis in Streptomyces are often clustered, additional cosmid clones were isolated using the 2.09 kb BamHI fragment (Table 4) from pVE650 to probe the S. avermitilis cosmid library. One cosmid, pVE924, spans the 24 kb of DNA between the avrA clone, pAT1, and pVE650. Thus, the cloned avermectin genes, avrA and the aglycone genes avrB, avrC and avrD, define an avermectin gene cluster spanning over 55 kb. Another cosmid, pVE923, extends past the avrA region, away from the aglycone region, about 20 kb. Collectively, over 110 kb of DNA has been isolated from the avermectin gene cluster region. These plasmids were mapped relative to each other by determining which BamHI fragments were contained in common to one or more plasmids, by Southern analysis to determine which plasmids contained BamHI fragments of the Group 1 and Group 2 sets of related sequences, and via Southern analysis to test for the presence on the plasmids of several fragments from the various plasmids. The relative location of pAT1, pVE650, and four cosmid clones is indicated in FIG. 3.

pVE859 contains 6 BglII fragments of approximately 0.9 kb, 1.8 kb. 4.7 kb, 5.4 kb, 14 kb, and 18 kb. The 14 kb fragment was cloned into the unique BglII site of pVE616, a 4.2 kb Amp$^r$ Thio$^r$ derivative of pBR322 with unique BamHi, BglII, PstI and HpaI cloning site. pVE616 is incapable of replicating in Streptomyces, but if it contains homologous DNA it can integrate into the genome by recombination resulting in Thio$^r$ derivatives. A derivative which contained the BglII fragment, pVE930, was digested with a mixture of BglII and EcoRI restriction enzymes and compared to pVE650 DNA digested with the same enzyme mixture. After separation on agarose gels and visualization by UV illumination it was observed that pVE650 and pVE930 contained a comigrating 1.55 kb BglII-EcoRI fragment. This establishes that in the genome of S. avermitilis the 14 kb BglII fragment cloned on pVE859 is adjacent to the 0.14 kb BglII fragment cloned on pVE650. The 14 kb BglII fragment was subsequently subcloned into the BamHI site of pIJ922 to yield pVE941. This plasmid was transformed into the aglycone producing mutants not complemented by pVE650 and complementation was observed. In addition, MA6316, a GMT− mutant was complemented by pVE941, the gene altered in the GMT− strain is designated avrF. Thus, all the tested aglycone mutants can be complemented by DNA on pVE650 and on pVE941, which collectively contain about 37 kb of S. avermitilis DNA.

A 12 kb PstI fragment from pVE859 has been subcloned onto pVE1043 at a unique PstI site, creating pVE1116. pVE1043 is a derivative of pIJ922 in which the region from EcoRI to BamHI has been replaced with a poly linker with unique sites for EcoRI, HpaI, PstI, NheI, AseI, HindIII, DraI, and BamHI. Plasmid pVE1116, containing the 12 kb PstI fragment, was introduced into mutants of all aglycone producing classes and the GMT mutants. As indicated in Table 2, biosynthesis of natural avermectins was observed in all mutants tested. Since this plasmid complements all mutants altered in glycosylation of avermectin, it presumably contains all the genes for glycosylation of avermectin. Additional restriction fragments were subcloned onto pVE1043 and introduced into the mutants for complementation studies, pVE1018 contains the 4.0 kb BamHI fragment from pVE941 and pVE1420 contains the 3.8 kb PstI-EcoRI fragment from pVE1116. The results are shown in Table 2. The defects in mutants MA6057 and MA6622 are assigned to avrE, the defects in MA6592 and MA6594 are designated avrG, and the defect in MA6590 is designated avrH. It is quite possible that some complementation classes will be found to contain more than one gene. FIG. 6 shows a restriction map of parts of pVE650, pVE941, and pVE1116 and the location of the 7 avermectin genes involved in glycosylation.

Interestingly, pVE923, which was isolated with the 2.09 kb BamHI probe, does not contain DNA that overlaps the 2.09 kb BamHI fragment probe. Plasmid pVE923 was isolated because it contains two other related sequences of Group 1. The four plasmids pVE923, pVE924, pVE855 and pVE859 have been inserted into strains of *Escherichia coli* using standard techniques and the cultures deposited to ensure availability. The four *E. coli* strains containing the 4 cosmid clones have been designated MB5373 (pVE923) deposited as ATCC 67891; MB5374 (pVE924) deposited as ATCC 67892; MB5370 (pVE855) deposited as ATCC 67889; and MB5372 (pVE859) deposited as ATCC 67890. The sizes of the BamHI fragments in these 4 cosmids, as well as pAT1 and pVE650, have been determined and are presented in Table 5.

Mapping cosmid pVE924 by constructing subclones of pVE924

Cosmid pVE924 spanned the region from pVE650 to pAT1. Since genes for antibiotic biosynthesis are often clustered, it was possible that other avermectin genes would be linked to the genes for O-methylation and glycosylation. The test this hypothesis the BamHI fragments form pVE924 were subcloned onto pVE616, pVE1053 (a derivative of pVE616), or pVE623 (a derivative of pIJ922). pVE924 was partially digested with BamHI and cloned into the uniqued BamHI site of the above three vectors. A set of clones containing 1 or more BamHI fragments was isolated. From the clones with more than one BamHI fragment, a map of the relative order of BamHI fragments was determined. FIG. 5 displays the restriction map of the BamHI fragments from pVE924.

Isolation of genes involved in synthesis of the avermectin macrocyclic lactone ring Five subclones of pVE924 (indicated by an * in FIG. 5) which collectively represent the DNA of pVE924, as well as plasmids pAT1, pVE650 and pVE941 were used in complementation experiments with 24 avermectin non producers (Avr), two C-22, C-23 dehydrase (DH) mutants, and a mutant unable to close the avermectin furan ring (FUR). Twelve mutants were complemented, including the DH, FUR and 9 Avr mutants. These mutants formed 8 complementation classes. The DH mutants represent avrI and FUR mutant represents avrJ. The 6 classes of nonproducers represent avrK, avrL, avrM, avrN, avrO, and avrP. The location of these genes is indicated on FIG. 3.

These results clearly show the DNA cloned on pVE923, pAT1, pVE924, pVE855, pVE650 and pVE859 contain many avermectin genes. Subcloning of all the DNA from this avermectin gene cluster will allow identification of the genes for avermectin biosynthesis.

Isolation of additional DNA from the avermectin gene cluster

A comparison of the restriction maps of pAT1, pVE923 and pVE924 showed that the region adjacent to the 0.55 kb BamHI fragment was different in the three clones. On pAT1, a 3.4 kb BamHI to vector juction fragment, which contains an EcoRI site, maps adjacent to the 0.55 kb BamHI fragment. On pVE924 a 3.2 kb BamHI fragment without an EcoRI site is located adjacent to the 0.55 kb BamHI fragment. Cosmid pVE923 has a 7.0 kb BamHI fragment located adjacent to the 0.55 kb BamHI fragment. In order to determined the actual structure of this region of the avermectin gene cluster, DNA from the *S. avermitilis* chromosome was directly cloned into *E. coli*.

This method relied on the homologous recombination system of *S. avermitilis* to direct the integration of an *E. coli* plasmid containing two fragments of the avermectin cluster which flank the region of interest. This plasmid, pVE1299, is a derivative of pVE616 (Thio$^r$) which contains the 3.4 kb BamHI fragment of pAT1, a 2.9 kb neomycin-resistance gene (neo) fragment form Tn5, and the 3.7 kb BamHI fragment from pVE924. The vector can not replicate in *S. avermitilis*. Upon transformation into *S. avermitilis*, transformants containing the plasmid integrated in the chromosome were isolated as Thio$^r$, Neo$^r$. After excision of this vector from *S. avermitilis* by recombination, the resulting plasmid DNA was isolated and used in transformation of *E. coli*. Plasmids were recovered in which the neo DNA was replaced with *S. avermitilis* DNA that is located between the two fragments originally cloned on pVE1299. Restriction mapping of one such plasmid, pVE1446, revealed that there were actually three chromosomal BamHI fragments (7.0 kb, 7.4 kb, and 8.0 kb) between the 0.55 and 3.7 kb BamHI fragments. Table 6 presents a restriction map of over 95 kb of DNA from the avermectin gene cluster region.

BRIEF DESCRIPTION OF THE DRAWINGS

FIG. 7. Restriction map of pVE1011. The ** mark the cloning sites used to form pVE1299.

Figure 1:
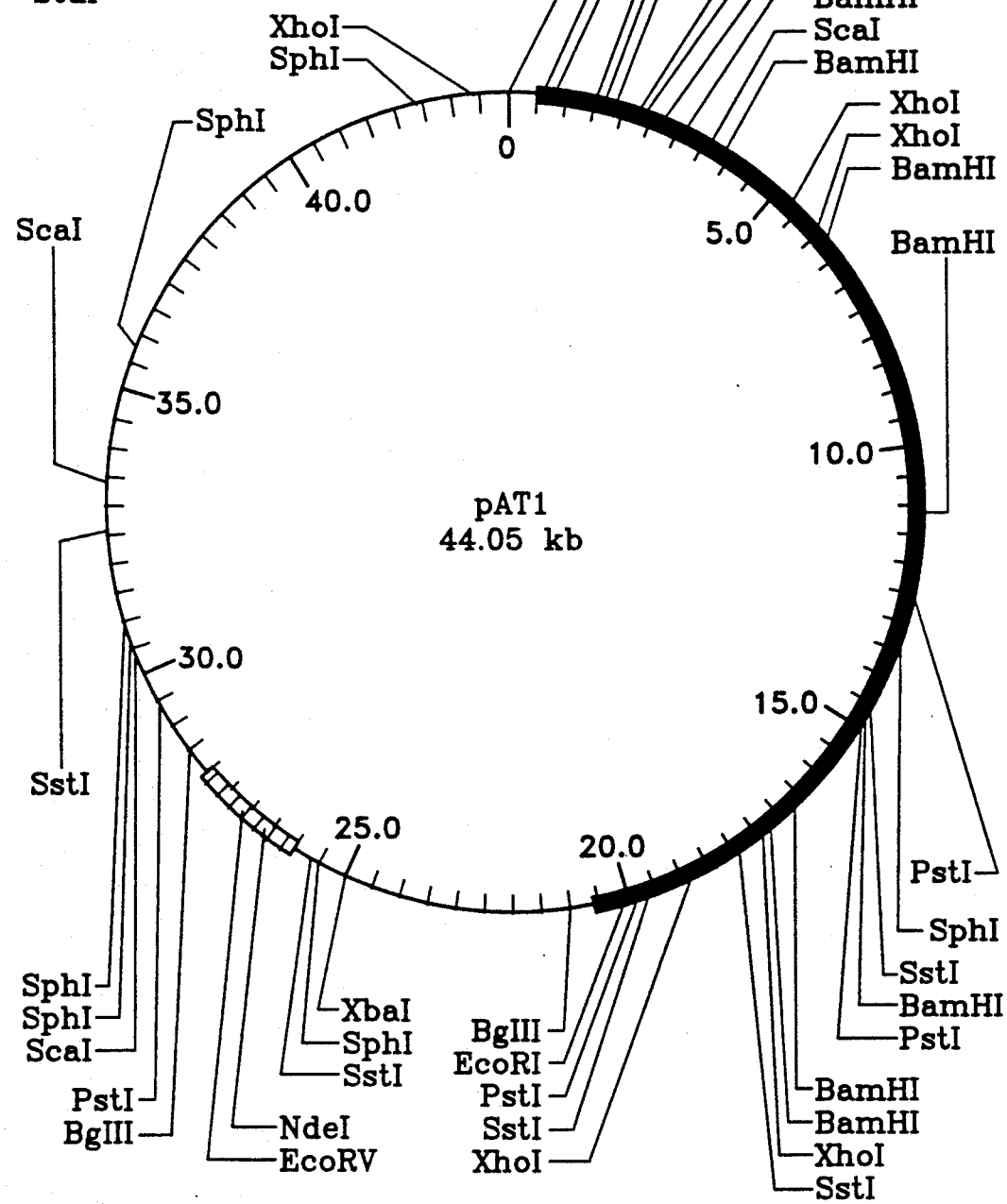
FIG. 1. Restriction map of pAT1. Only the sites mapped in both the vector and insert DNA are indicated.

This application describes the successful cloning of avermectin genes using low copy number vectors to complement *S. avermitilis* mutants blocked in avermectin biosynthesis. In U.S. Pat. No. 4,703,009 an example of how to clone genes for avermectin biosynthesis in a high copy number vector was described but this description is flawed. First such described high copy number vectors will not replicate successfully with large fragments. Second such high copy number vectors which contain *S. avermitilis* inserts apparently undergo recombination with the genome. These plasmids are difficult to isolate and characterize. Third high copy number clones alter the regulation of avermectin genes which makes detection of complementing clones difficult.

UTILITY

The avermectin gene cluster region from *S. avermitilis*, which has been cloned on several plasmids, can be used to create new processes to produce avermectins, can be used to produce new avermectins, and can be used to create hybrid antibiotics. Several of the genes required for avermectin biosynthesis have been localized by subcloning. Other avermectin genes are located within the region cloned here and/or near the region cloned here. There are many uses for the cloned *S. avermitilis* DNA.

Cloned avermectin biosynthesis genes may be used to alter the normal composition of the 8 natural product avermectins, resulting in new processes. Introduction of the C-5 O-methyltransferase gene, which has been subcloned from the avermectin gene cluster region, into *S. avermitilis* strains, results in the enhanced production of C-5 methoxy components. Similarly, the gene for avermectin C-22, C-23 dehydrase can be introduced into *S. avermitilis* strains to enhance the production of dehydrated components.

Identification, from the region cloned here, of a gene encoding an enzyme which is a rate limiting step in avermectin biosynthesis, can be used to create an improved process for avermectin production. This would occur by subcloning the gene and manipulating it to increase the expression of the limiting enzyme.

Novel avermectins can be produced by mutagenesis of the cloned genes. Mutagenesis of the glycosylation genes can yield strains which produce predominately monosacharide containing avermectins. Mutagenesis of the genes for the synthesis of the avermectin aglycone can result in novel avermectins. Avermectin is synthesized by the sequential addition of short chain carboxylic acids which may retain a keto group or the keto group may be reduced to a different functional group such as a hydroxyl, a double bond or a saturated bond. Mutagenesis of the cloned avermectin genes can result in the synthesis of avermectin with a different carboxylic acid than the natural avermectins, or avermectins with different functionalities.

The DNA from the avermectin gene cluster region can be used as a hybridization probe to identify homologous sequences. Thus, the DNA cloned here could be used to locate additional plasmids from the *S. avermitilis* gene libraries which overlap the region described here but also contain previously uncloned DNA from adjacent regions in the genome of *S. avermitilis*. In addition, DNA from the region cloned here may be used to identify non-identical but similar sequences in other organisms. The genes for avermectin glycosylation can be used to identify and isolate genes involved in glycosylation of other antibiotics. The gene for C-5 avermectin O-methyltransferase can be used as a DNA probe to identify other O-methyltransferase genes and aid in their cloning. The introduction of these heterologous genes into *S. avermitilis* can result in potent anthelmintics by the synthesis of novel avermectins with altered methylation or glycosylation. Similarly, DNA containing genes for the synthesis of the avermectin aglycone can be used as a probe to identify, and subsequently clone, sequences for similar macrolides. The genes for other anthelmintics such as milbemycins could also be cloned in this way. The complementation *S. avermitilis* mutants with the appropriate genes from the milbemycin producing strains can result in potent, hybrid anthelmintic compounds.

The following examples are provided in order that the invention might be more completely understood. They should not be construed as limitation of the invention.

EXAMPLE 1

Isolation, Maintenance and Propagation of Plasmids

The plasmid DNA was isolated and handled by procedures differing little from those established by work on other plasmids. A good procedures manual is T. Maniatis, E. F. Fritsch, and J. Sambrook, *Molecular Cloning: a Laboratory Manual*, Cold Spring Harbor Laboratory, Cold Spring Harbor, N.Y. (1982). A good procedures manual for Streptomyces is D. A. Hopwood, M. J. Bibb, H. F. Chater, T. Kieser, C. J. Bruton, H. M. Kieser, D. J., Lydiate, C. P. Smith, J. M. Ward, and H. Schrempf, *Genetic Manipulation of Streptomyces, a Laboratory Manual*, John Innes Foundation, Norwich, UK (1985). The specific procedures used in this work are described herein, unless they are identical to those given in the above mentioned manuals.

A. Growth of Streptomyces for Plasmid Isolation.

Single colonies of Streptomyces strains were isolated on R2YE, medium A or medium D. R2YE containing 103 g sucrose, 10 g glucose, 3 g yeast extract, 3 g proline, 0.1 g casamino acids, 0.25 g $K_2SO_4$, 10.1 g $MgCl_2.6H_2O$, 2 ml of R2 trace elements (0.2 g $FeCl_3.6H_2O$, 0.04 g $ZnCl_2$, 0.01 g $MnCl_2.4H_2O$, 0.01 g $CuCl_2.2H_2O$, 0.01 g $NaB_4O_7.10H_2O$, and 0.1 g $(NH_4)_6Mo_7O_{24}.4H_2O$ per liter) and 15 g agar brought to a final volume of 940 ml with distilled water. After autoclaving, the following solutions were added to each liter of medium: 10 ml of 0.5% $NH_4PO_4$, 8 ml of 2.5M $CaCl_2$, and 40 ml of 0.2M TES pH 7.2 (N-tris-(hydroxyethyl) methyl-2-amino ethanesulfonic acid). Medium D contained 4 g yeast extract, 10 g malt extract, 4 g glucose, 5 ml of trace elements (50 ml of 37.3% HCl, 61.1 g $MgSO_4.7H_2O$, 2.0 g $CaCO_3$, 5.4 g $FeCl_3.6H_2O$, 1.44 g $ZnSO_4.7H_2O$, 1.11 g $MnSO_4.H_2O$, 0.25 g $CuSO_4.5H_2O$, 0.062 g $H_3BO_3$ and 0.49 g $Na_2MoO_4.2H_2O$ per liter), and 15 g agar per liter. The pH of medium D was adjusted to pH 7.0 with NaOH before autoclaving. Liquid growth medium for Streptomyces was YEME (3 g yeast extract, 5 g peptone, 3 g malt extract, 10 g glucose per liter) modified to contain 30% sucrose, 5 mM $MgCl_2$ and included antibiotics to select for the maintenance of plasmids. Strains with plasmids containing a thiostrepton-resistance gene (tsr) were grown with 5 mg per ml of thiostrepton. A single colony was inoculated into 6 ml of YEME in a 10 mm by 150 mm tube. The culture was grown for 3 days at 28° C. with shaking at 220 rpm.

(1) Small scale plasmid isolation.

For small scale plasmid preparations, mycelia from the 6 ml YEME culture were collected by centrifugation at 14,000×g for 12 minutes. The pellet was washed once in 10% sucrose, 10 mM ethylenediamine tetraacetate (EDTA), pH 8.0. Plasmid DNA was isolated from the mycelia by a rapid boiling procedure described previously by MacNeil, D. J., *J. of Microbiol. Methods* pg 115-123, (1986). The pellet was resuspended in 0.5 ml of STET (8% sucrose, 5% Triton X-100, 50 mM EDTA and 50 mM Tris, pH 8.0), 30 μl of a 30 mg/ml lysozyme (Sigma, St. Louis, Ma.) solution was added, the mixture was incubated for 15 minutes at 37° C., and then placed in a boiling water bath for 2 minutes. The boiled lysate was spun at 14,000×g for 12 minutes, the supernatant was removed to a 1.5 ml Eppendorf tube, and then extracted once with phenol previously equilibrated with TE (10 mM Tris, 1 mM EDTA, pH 7.9). The aqueous phase was removed to another 1.5 ml Eppendorf tube, an equal volume of isopropanol was added, the solutions were incubated at −20° C. for 20 minutes, and the DNA was pelleted at 7000×g for 6 minutes. After washing once in 70% ethanol, the DNA was resuspended in 100 μl of TE. An estimated 2 to 10 μg of plasmid DNA was obtained from a 6 ml culture. Alternatively, plasmid DNA was isolated from 6 ml cell pellet by an alkaline lysis procedure. The cell pellet was resuspended in 1 ml of 50 mM glucose, 25 mM Tris pH 8, 10 mM EDTA, and 50 μl of a 30 mg/ml lysozyme solution in 50 mM glucose, 25 mM Tris pH 8, 10 mM EDTA was added. Following incubation for 15 minutes at 37° C., 1.5 ml of a 0.2N NaOH, 1% SDS solution was added, the mixture was vortexed for 5 seconds and the mixture was incubated for 15 minutes on ice. Next 150 μl of ice cold pH 4.8 potassium acetate solution (5M with respect to acetate, 3M with respect to potassium) was added, the mixture vortexed for 10 seconds, and incubated on ice for 15 minutes. The mixture was centrifuged for 15 minutes at 12,000×g, at 4° C. and the resulting supernatant was transferred to a new tube. 2.5 ml of −20° C. isopropanol or isopropanol containing 0.05% diethyl pyrocarbonate was added, mixed, and centrifuged at 12,000×g for 15 minutes at 4° C. Remaining solvent from the resulting DNA pellet was removed in a Savant Speed Vac, and the DNA was dissolved in 0.5 ml of 0.3M ammonium acetate. The solution was transferred to a 1.5 ml Eppendorf tube, mixed with 400 μl of phenol, previously equilibrated with 1M Tris pH 7.9, and the aqueous phase separated by centrifugation in a microfuge for 3 minutes. The aqueous phase was removed to another Eppendorf tube and the phenol extracted with 400 μl of chloroform. The resulting aqueous DNA solution was precipitated with 2 volumes of ethanol at −70° C. for at least 20 minutes. The DNA was collected by centrifugation in a microfuge for 15 minutes, washed once with −20° C. 70% ethanol, dryed in a Savant Speed Vac, and resuspended in 100 μl of TE buffer.

(2) Large Scale plasmid isolation.

For large scale plasmid isolations a 6 ml YEME culture was used to inoculate a 250 ml baffled flask containing 30 ml of YEME. After 2 days of shaking at 28° C. at 220 rpm the culture was used to inoculate a baffled 2 liter flask containing 500 ml of YEME. The mycelia were harvested by centrifugation at 4,000×g for 15 minutes and were washed once in 10% sucrose, 10 mM EDTA. Plasmid DNA was isolated from the mycelia by either of two methods. One method was a rapid boiling procedure as described previously by MacNeil, D. J., 1986, supra. The cell pellet was resuspended in 40 ml of STET, and 0.5 ml of 50 mg/ml lysozyme solution in 0.1M Tris pH 7.9 was added. The suspension was incubated at 37° C. for 20 minutes, placed in a boiling water bath for 3 minutes and centrifuged at 90,000×g for 30 minutes at 4° C. The supernatant was removed, one half volume of −20° C. isopropanol was added, mixed and incubated at −20° C. for 20 minutes. DNA was collected by centrifugation at 9,000×g for 8 minutes. The DNA was resuspended in 13 ml of a CsCl solution prepared by dissolving 78 g of CsCl into 65 ml of 0.1M Tris, 0.01M EDTA, pH 7.9 and adding 2 ml of ethidium bromide (5 mg/ml). The mixture was centrifuged at 43,000 rpm in a Beckman ultracentrifuge for 44 hours. The second method to isolate plasmid DNA was a modification of the alkaline lysis procedure described by Maniatis et al., 1982, supra. The 500 ml cell pellet was resuspended in 30 ml of 50 mM glucose, 25 mM Tris pH 8, 10 mM EDTA and 2 ml of 15 mg/ml lysozyme solution was added. The mixture was swirled occasionally during incubation at 37° C. for 30 minutes. 50 ml of 0.2N NaOH, 1% SDS, was added and the mixture was mixed with a 1 ml pipet until the mixture appeared homogeneous and lysis was evident. After incubation on ice for 25 minutes with occasional swirling, 40 ml of 5M potassium acetate pH 4.8 was added and mixed until the precipitated material was dispersed into small clumps. After incubation on ice for 25 minutes, the mixture was centrifuged at 15,000×g for 15 minutes at 4° C. The plasmid containing supernatant was added to 72 ml of −20° C. isopropanol mixed and centrifuged at 15,000×g for 15 minutes at 4° C. The resulting supernatant was discarded, excess liquid was removed with a sterile cotton swab and the DNA pellet dryed further under vacuum for 5 minutes. The DNA was resuspended in 9 ml of 20 mM Tris, 0.5% sarkosyl, 5 mM EDTA, pH 7.9 plus 25 μl of 10 mg/ml RNase, the volume was brought up to 10 ml, 11 g of CsCl was added and 1 ml of a 5 mg/ml solution of ethidium bromide was added. After centrifugation at 5000×g for 5 minutes the supernatant was added to a Beckman Quick Seal tube, sealed and spun at 65,000 RPM in Beckman 70.1 Ti rotor for 17.5 hours at 20° C. The plasmid DNA band, obtained from either method, was visualized by UV illumination, was removed and rebanded in 13 ml of a CsCl solution prepared by dissolving 71 g of CsCl into 65 ml of 0.1M Tris, 0.01M EDTA, pH 7.9 and adding 0.2 ml of ethidium bromide (5 mg/ml). The plasmid DNA was removed from the second gradient and ethidium bromide was removed by 4 isopentyl alcohol extractions. The plasmid DNA was precipitated by adding 2 volumes of TE, 0.3 volumes of 3.5M sodium acetate, and 6 volumes of 100% ethanol. After overnight incubation at −20° C. the DNA was pelleted by centrifugation at 13,000×g for 12 minutes, washed once with 70% ethanol, and resuspended in 1 ml of TE. The yield of DNA from 500 ml of cells was 200 to 1000 μg.

B. Growth of *E. coli* for plasmid isolation.

*E. coli* cultures containing pVE328-derived cosmid clones were grown in LB-Amp medium (10 g tryptone, 5 g yeast extract, 5 g, NaCl per liter containing 100 μg/ml of ampicillin). These cultures were grown at 37° C. shaking at 220 rpm when the $OD_{600}$ was between 1.0 to 2.0, 0.5 ml of 50 mg/ml chloramphenicol was added. Incubation continued overnight at 37° C. Large amounts of plasmid DNA (200 to 1,500 μg) were prepared from a 500 ml culture by a modification of the alkaline lysis procedure described above for Streptomyces. Cells were collected at 6,000×g for 6 minutes, the cell pellet was resuspended in 18 ml of 50 mM glucose, 25 mM Tris pH 8, 10 mM EDTA and 2 ml of 15 mg/ml lysozyme solution added. The mixture was swirled occasionally during incubation at room temperature for 15 minutes. Forty ml of 0.2N NaOH, 1% SDS, was added and the mixture was mixed with a 1 ml pipet until the mixture appeared homogeneous and lysis was evident. After incubation on ice for 25 minutes with occasional swirling, 20 ml of 5 M potassium acetate pH 4.8 was added and mixed until the precipitated material was dispersed into small clumps. After incubation on ice for 25 minutes the mixture is centrifuged at 15,000×g for 15 minutes at 4° C. The plasmid containing supernatant was added to 50 ml of −20° C. isopropanol, mixed, and centrifuged at 15,000×g for 15 minutes at 4° C. The resulting supernatant was discarded, excess liquid was removed with a sterile cotton swab, and the DNA pellet dried further under vacuum for 5 minutes. The DNA was resuspended in 9 ml of 20 mM Tris, 5 mM EDTA, pH 7.9 plus 25 μl of 10 mg/ml RNase, the volume was brought to 10 ml, 11 g of CsCl was added and 1 ml of a 5 mg/ml solution of ethidium bromide was added. After centrifugation at 5000×g for 5 minutes, the supernatant was added to a Beckman Quick Seal tube, sealed, and spun at 65,000 RPM in Beckman 70.1 Ti rotor for 17.5 hours at 20° C. The plasmid DNA band was visualized by UV illumination, removed, and rebanded in 13 ml of a CsCl solution prepared by dissolving 71 g of CsCl into 65 ml of 0.1M Tris, 0.01M EDTA, pH 7.9 and adding 2 ml of ethidium bromide (5 mg/ml). The plasmid DNA was removed from the second gradient and ethidium bromide was removed by 4 isopentyl alcohol extractions. The plasmid DNA was precipitated by adding 2 volumes of TE, 0.3 volumes of 3.5M sodium acetate, and 6 volumes of 100% ethanol. After overnight incubation at −20° C., the DNA was pelleted by centrifugation at 13,000×g for 12 minutes, washed once with 70% ethanol and resuspended in 1 ml of TE.

C. Restriction analysis of plasmid DNA.

Procedures for restriction analysis of DNA and agarose gel electrophoresis as well as other standard techniques of recombinant DNA technology are thoroughly described in T. Maniatis, E. F. Fritsch, and J. Sambrook, *Molecular Cloning: a Laboratory, Manual*, Cold Spring Harbor Laboratory, Cold Spring Harbor, N.Y. (1982). Plasmid DNA isolated from large and small scale preparations was cleaved with various restriction enzymes according to the manufacture's directions. Enzymes were obtained from New England Biolabs (Beverly, Mass.), Bethesda Research Labs (Bethesda, Md.), and IBI (New Haven, Conn.). The digestions were analyzed by electrophoresis in 0.8% agarose using 0.08M Tris-acetate-0.004M EDTA as a buffer. The size of the fragments was determined by comparison to fragments of phage lambda DNA of known molecular weight.

D. Mapping restriction enzyme sites in cloned DNA.

The location of restriction sites in pAT1 and pVE650 was determined by standard mapping techniques. These included analysis of single and double enzyme digestions, by subcloning and analysis of the subclones, and by analysis of the fragments contained on various cosmids isolated from the region. The size of the fragments was determined by comparison to lambda fragments digested with HindIII or a combination of BamHI and EcoRI.

E. Transformation of Streptomyces by plasmid DNA.

(1) Protoplast formation.

Transformation was accomplished by PEG-mediated DNA uptake by protoplasts. Protoplasts of *S. avermetilis* were prepared as described by MacNeil, D. J. and Klapko, L. M., 1987, *J. Indust. Microbiol.* 2: 209-218. Thirty ml of YEME medium containing 30% sucrose, 5 mM MgCl$_2$ and 0.5% glycine was inoculated with $5 \times 10^7$ spores of *S. avermitilis*, or with 1 ml of 6 ml YEME culture. (The YEME culture was prepared by inoculating a single colony into 6 ml of YEME containing 30% sucrose, 5 mM MgCl$_2$, and 0.5% glycine). The 30 ml culture was grown for 2 or 3 days at 28° C., the mycelia were pelleted at 14,00×g for 12 minutes and washed once with P medium. P medium contains 103 g sucrose, 0.25 g K$_2$SO$_4$, 2.03 g MgCl$_2$.H$_2$O, and 2 ml of R2 trace elements per liter. After autoclaving the following additions were made; 10 ml of 0.5% KH$_2$PO$_4$, 8 ml CaCl$_2$.2H$_2$O, 40 ml of 0.2M MES (2-(N-morpholino)ethanesulfonic acid). The mycelium was resuspended in 15 ml of P medium, 0.2 ml of lysozyme (50 mg/ml in P medium) was added, and the suspension was incubated at 37° C. for 1 hour with slow shaking. Protoplasts were separated from undigested mycelium by filtering the mixture through 2 cm of glass wool in the bottom of a 10 ml syringe. The protoplasts were pelleted at 6,000×g for 6 minutes and resuspended in 3 ml of P medium which contained 20% sucrose. Protoplasts of *S. lividans* were prepared as described above for *S. avermitilis*, except TES (pH 7.2) was used in all buffers instead of MES. All protoplasts were quick frozen in a dry ice/ethanol bath and stored at −70° C.

(2) Transformation procedure.

Streptomyces strains were transformed by modification of the method described for *S. avermitilis* (MacNeil and Klapko, 1987, supra). A quantity of 0.1 ml of protoplasts (approximately 10$^9$/ml) were mixed with 5–10 μl of plasmid DNA (25 ng–1 μg), 0.5 ml of medium T was added and the mixture incubated for 30 seconds at room temperature. On some occasions half as much protoplasts, DNA, and medium T were mixed together. Medium T is similar to medium P except it contains different concentrations of sucrose (2.5%), CaCl$_2$ (0.1M) and is buffered with 50 mM Tis-maleic acid (pH 8) and has 25% (wt.vol) PEG 1000. The mixture was serially diluted in P medium containing either 0.01M MES for *S. avermitilis* or 0.01M TES for *S. lividans*. For *S. lividans*, 100 μl of the dilutions of the transformation mixtures were spread on R2YE medium containing 17% sucrose. For *S. avermitilis* 100 μl of the dilutions of the transformation mixtures were added to 3 ml of RM14 soft agar at 50° C. and poured onto RM14 plates. RM14 is similar to R2YE except it contains 205 g sucrose, 20 g agar, 3 g of oatmeal agar per liter, and 0.1M MES (pH 6.5) instead of TES. RM14 soft agar contains only 6 g of agar per liter.

(3) Detection of transformation.

R2YE and RM14 regeneration media containing the transformed protoplasts were incubated for 20 hours at 28° C. Regeneration plates were overlayed with 3 ml of RM14 soft agar containing 0.5 mg of thiostrepton. Transformants appeared on the regeneration plates in 4 to 15 days.

E. Transformation of *E. coli* by plasmid DNA.

Competent cells of *E. coli* were prepared by the method of Mandel, M. and Higa, A., *J. Mol. Biol.*, 53 pg 154–162 (1970). Cells were grown in LB medium to an $A_{600}=0.45$ and incubated on ice 20 minutes. Cells were pelleted and resuspended to one-half their original volume in 0.1M $CaCl_2$. After 20 minutes on ice, cells were again pelleted and resuspended to 0.1 of their original volume in 0.1M $CaCl_2$. These competent cells were made 15% glycerol and stored at −70° C.

For transformations, 0.2 ml of competent cells was mixed with 10 μl of DNA (10 to 1000 ng/ml). The mixture was incubated on ice for 10 minutes then at 37° C. for 3 minutes. A quantity of 0.5 ml of LB medium was added and the culture was shaken at 37° C. at 220 RPM for 1 hour. Aliquots were plated on LB plates with 100 μg/ml of ampicillin to select for the plasmids.

F. Subcloning fragments into pIJ922 for complementation tests

To aid in locating genes for avermectin biosynthesis DNA fragments from pAT1, pVE650 and pVE859 were subcloned onto pIJ922. Two to ten micrograms of pIJ922 were linearized at the unique BamHI or EcoRI sites in pIJ922 by digestion with the appropriate restriction enzyme. The linear DNA was treated with calf intestinal alkaline phosphatase (CIAP) (Boehringer Mannheim, Indianapolis, Ind.) as described by the manufacturer or by alternative procedures. A simple method was to treat the linearized pIJ922 immediately after the completion of the restriction enzyme digestion. CIAP, (0.02 units per μg of DNA) was added directly to the restriction enzyme digestion mixture and incubated for 30 minutes at 37° C. A second aliquot of CIAP was added and the digestion continued for another 30 minutes. The reaction was terminated by the addition of 1/5 volume of 100 mM EDTA, 25% glycerol, 0.25% bromephenol blue, 0.2% SDS. The linear vector was electrophoresed on a 0.8% agarose gel and the linear DNA was electro-eluted from the agarose slice containing the DNA. The DNA was ethanol precipitated and resuspended in 50 to 100 μl of TE. For subcloning, 5 to 10 μg of pAT1, pVE650 or pVE859 were digested with a restriction enzyme BamHI, BglII, PstI or, EcoRI, electrophoresed in a 0.8% agarose gel, electroeluted, ethanol precipitated and resuspended in 50 to 100 μl of TE. Various aliquots of the BamHI linearized vector and BamHI or BglII digested fragments, or EcoRI linearized vector and EcoRI digested fragment, or PstI linearized vector and PstI digested fragment, were ligated and transformed into S. lividans. Thio$^r$ transformants were selected and tested for the presence of the fragment of interest by minilysate analysis of 6 ml YEME grown cultures. Derivatives with the appropriate insert were saved and 5 to 10 μl of the minilysate were transformed into various S. avermitilis mutants, and the resulting thiostrepton-resistant transformants tested for complementation of the mutant defect.

EXAMPLE 2

Isolation and characterization of pAT1

A. Construction of a S. avermitilis DNA library.

A library of S. avermitilis DNA was made by ligating genomic DNA partially digested with Sau3A restriction enzyme into the compatible and unique BamHI site of pIJ922. pIJ922 is a 24 kb, low copy number, Streptomyces vector which can be selected as Thio$^r$ in Streptomyces (see Hopwood et al., *Genetic Manipulations of Streptomyces a Laboratory Manual*, pg 279).

(1) Isolation of Genomic DNA.

An S. avermitilis spore stock was prepared by spreading 0.1 ml of a visibly turbid YEME grown culture onto Medium D agar plates. After 5 to 15 days the spores are removed with a cotton swab, wetted with 0.85% NaCl, 50% glycerol and transferred to 2 ml of 0.85 NaCl, 50% glycerol. 100 μl of the S. avermitilis spore stock (ca. $5\times10^9$ spore/ml) was inoculated into a 250 ml baffled flask containing 30 mls of YEME+30% sucrose+0.5% glycine. After 4 days incubation at 27° C. on a rotary shaker at 220 rpm, the cells were harvested by centrifugation at 12,000×g for 10 minutes at 4° C. using a 25 ml Corex centrifuge tube. The cell pellet was resuspended in 20 ml of P medium containing 0.01M MES, pH 6.5, centrifuged at 12,000×g for 10 minutes at 4° C., and the pellet was resuspended in 5 ml of P medium, 10 ml of lysozyme was added and mixed. The suspension was incubated at 37° C. for 1 hour and then 2.5 ml of 0.25M EDTA, pH 8.0 was added and the incubation continued on ice for 15 minutes. Cell lysis was evident after the addition of 7.5 ml of 2% sarkosyl by gently swirling the mixture. Following an additional 30 minute incubation on ice, 150 μl of a solution of preboiled, 5 mg/ml RNAse Type 1A (Sigma, St. Louis, Mo.) was added and incubation continued for 1 hour at 37° C. Next, 0.6 ml of Proteinase K (IBI, New Haven, Conn.) was added and the mixture was incubated for 2 hours at 37° C., then incubated at 4° C. overnight. (Proteinase K was predigested by incubating a 25 mg/ml solution at 37° C. for 1 hour). Fifteen ml of phenol, previously equilibrated with 0.2M Tris, pH 7.9, was added to the lysate and mixed at 8 rpm on a rotating mixer (Rugged Rotator, Kraft Devices, Mineola, N.Y.). After spinning the mixture in a table top centrifuge, the aqueous layer was transferred to a new tube and the extraction repeated 2 more times. Phenol was removed from the sample by 5 extractions with chloroform:isoamyl alcohol, 24:1. To the resulting aqueous solution, 0.5 volumes of 7.5M ammonium acetate were added, mixed, and 2 volumes of ice-cold ethanol were added. Using a glass rod, the ethanol was mixed and the resulting precipitated DNA spooled on to the rod. Excess solution was removed from the DNA by pressing the rod against the side of the tube, and the DNA was dissolved in 5 ml of TE containing 4 μl of diethyl pyrocarbonate. The DNA was dissolved overnight while rotating at 8 rpm on the rotating mixer. The DNA was then again precipitated from the solution as described above and finally dissolved in 2.0 ml of TE to yield 469 μg/ml of DNA as determined by the $OD_{260}$ measurement.

(2) Size fractionation of the genomic DNA.

After a pilot experiment to determine conditions to dilute MboI and Sau3A to yield a maximum of fragments in the 20 to 40 kb range, four aliquots of 100 mg of S. avermitilis DNA were digested at 37° C. with 10 U, 16.7 U, 23.3 U, and 30 U of MboI and four aliquots of 100 μg of S. avermitilis DNA were digested at 37° C. with 3 U, 5 U, 7 U, and 9 U of Sau3A in a 1 ml reaction mixture for 10 minutes. The same buffer, KCl Buffer, was used for both enzymes and it was 20 mM Tris, 20 mM KCL, 10 mM $MgCl_2$, 1 mM dithiothreitol, 100 μg/ml bovine serum albumin, pH 7.9. The reactions were terminated by addition of 0.25 ml of stop mix (1% SDS, 50 mM EDTA) followed by phenol extraction. Unless otherwise indicated, DNA solutions were treated with phenol to inactivate enzymes and remove protein. The standard phenol extraction consists of sequential extractions of the DNA solution with organic solvents followed by centrifugation to separate the phases. The extractions are done with equal volumes of phenol, previously equilibrated with 0.2M Tris pH 7.9; phenol:chloroform:isoamyl alcohol 25:24:1; chloroform:isoamyl alcohol 24:1. The DNA may be concentrated and/or the salts removed by ethanol precipitation. The standard ethanol precipitation of DNA consists of the addition of 0.5 volume 7.5M ammonium acetate, 3 volumes of ethanol, and incubation at −20° C. overnight or −70° C. for 1 hour. The DNA is pelleted by centrifugation at 12,000×g for 15 minutes, washed with 70% ethanol, dryed, and resuspended in TE. Following phenol extraction and ethanol precipitation, the MboI digestions were pooled and the Sau3A digestions were seperately pooled and loaded on a 32 ml 10% to 40% sucrose gradient (1M NaCl, 20 mM Tris, 5 mM EDTA, pH 8.0). After 21 hours of centrifugation in a Beckman SW 28 rotor at 26,000 rpm the gradient was punctured at the bottom and collected in 14 drop fractions. Ten μl from every third fraction was run on a 0.4% agarose gel and compared to the lambda standards. Fractions 19 to 23 of the MboI digestions were pooled into a 10–30 kb fraction and fractions 16 to 18 were pooled into >30 kb fraction. Fractions 23 to 26 of the Sau3A digestions were pooled into the 10–30 kb fraction and fractions 15 to 22 were pooled into a >30 kb fraction. The pooled fractions were dialysed against TE at 4° C. for 48 hours, concentrated to 2 ml with 2-butanol, and precipitated with ammonium acetate and ethanol at −20° C. overnight. The DNA was resuspended in 400 μl of TE, and phenol extracted including a final ethyl ether extraction, ethanol precipitated and resuspended in 100 μl of TE.

(3) Preparation of pIJ922.

pIJ922 was cleaved at its unique BamHI site and treated with calf intestine alkaline phosphatase (CIAP, Boehringer Mannheim, Indianapolis, Ind.). pIJ922 DNA was isolated from S. lividans TK54 by the rapid boiling method, as described in Example 1, from 4 liters of cells. Both TK54 and pIJ922 were obtained from D. Hopwood, John Innes Institute, Norwich England. 233 μg of pIJ922 DNA were obtained. pIJ922 was cleaved by BamHI in a reaction volume of 400 μl containing 40 μl of 10×KCl buffer, (200 mM Tris, 200 mM KCl, 100 mM MgCl$_2$, 1 mg/ml bovine serum albumin, pH 7.9)100 μl of pIJ922 (23.3 μg), 5 μl of BamHI restriction enzyme (10 U/μl), and 255 μl of H$_2$O. After digestion at 37° C. for 4 hours the DNA was treated with phenol and ethanol precipitated. The DNA pellet was resuspended in CIAP reaction mixture consisting of 100 μl of 10×CIP Buffer (0.5M Tris pH 9.0, 10 mM MgCl$_2$, 1 mM ZnCl$_2$, 10 mM spermidine) and 886 μl of H$_2$O. The reaction was begun by the addition of 7 μl of CIAP, 28 U/μl, after incubation at 37° C. for 30 minutes an additional 7 μl of CIAP was added. The reaction was terminated by the addition of 1 ml of stop mix (10×STE 200 μl [100 mM Tris pH 8.0, 1M NaCl, 10 mM EDTA], 10% SDS 100 μl, 0.5M EDTA pH 8.0 80 ml, and H$_2$O 620 μl) followed by heating at 65° C. for 10 minutes. The DNA was phenol extracted, concentrated to 1 ml with 2-butanol, ethanol precipitated and resuspended in 250 μl TE, ethanol precipitated again and resuspended in 100 μl of TE. Aliquots of the treated pIJ922 were run on 0.7% agarose gels and compared to known amounts of lambda DNA and pIJ922 cut with BamHI. This indicated that 12 μg had been recovered after the above treatments.

(4) Ligation of pIJ922 to S. avermitilis genomic fragments.

Before ligation, the pIJ922 and the S. avermitilis Sau3A fragments >30 kb were coprecipitated by mixing 5 μl of CIAP treated pIJ922, 15 μl of Sau3A fragments >30 kb, 10 μl of 3M sodium acetate, 80 μl of TE and 275 μl of ethanol. After overnight incubation at −20° C., the DNA pellet was resuspended in a mixture of 174 μl of H$_2$O, 25 μl of 10×ligase buffer (0.5M Tris pH 7.4, 100 mM MgCl$_2$, 10 mM spermidine, and 1 mg/ml BSA), 25 μl of 0.1M dithiothreitol, and 25 μl of 10 mM ATP). The ligation was begun by the addition of 1 μl of T4 DNA ligase (New England Biolabs, Beverly Ma) and incubation was at 13° C. overnight. In three experiments, S. lividans protoplasts were transformed with 10 μl of the ligation mix as described in Example 1, over 10,000 transformants were obtained. Among the transformants 4 were observed to produce melanin, a pigment produced by S. avermitilis but not S. lividans. The transformants were allowed to sporulate and the spores were collected. When the spores were plated for single colonies on R2YE and plasmid DNA was prepared it was observed that over 65% of the colonies contained inserts of an average size of about 20 kb. The spores were used to inoculate YEME medium and plasmid DNA was prepared by the rapid boiling method and purified as described in Example 1. This pIJ922-S. avermitilis library was used to isolate clones which complemented S. avermitilis avermectin mutants.

B. Isolation of pAT1, a plasmid with the gene for C-5 avermectin O-methyltransferase.

Protoplasts of MA6233, a strain deficient in C-5 avermectin O-methyltransferase (OMT−) and which makes predominantly avermectin B1a and B2a were transformed with the pIJ922-S. avermitilis library. The transformation mixture was plated on RM14 regeneration medium and incubated at 28° C. After overnight incubation Thio$^r$ transformants were selected by adding a 3 ml overlay of RM14 medium with 0.6% agar and containing 165 μg/ml of thiostrepton. After 12 to 16 days further incubation at 28° C. the transformants were individually patched onto sporulation Medium D using sterile toothpicks. After a further 5–7 days of incubation at 28° C., sporulation was evident. Next, a 0.25 inch filter disk (Schleicher & Schuell, analytical paper #740-E) was wetted with growth Medium E, rubbed across the sporulated patch and used to inoculate production Medium F. After 12–16 days incubation at 28° C., the mycelia were extracted with methanol, aliquots of the extract were applied to E. Merck Silica Gel 60 F-254 TLC plates and the avermectins developed for 14 minutes with a dichloromethane:ethyl acetate:methanol 9:9:1 solvent mixture. This solvent system resolves the 8 avermectins into four spots; the avermectin a and b components are not resolved and the order from fastest to slowest band is: avermectin A1, A2, B1, and B2. Under these conditions MA6233 produces two spots representing avermectin B1a+b and avermectin B2a+b. Over 10,000 transformants were screened for production of avermectin A1a+b and A2a+b. An isolate which contained pAT1 was found to produce four spots which co-chromatographed with avermectins A1a+b, A2a+b, B1a+b, and B2a+b. Plasmid DNA was isolated from this isolate and used to transform MA6233 and 5 other S. avermitilis mutants defective in C-5 O-methyltransferase. All six regained the ability to produce avermectin A1a+b and A2a+b. HPLC analysis of methanol extracts from mutants containing pAT1 confirmed the presence of avermectin A1a+b and A2a+b. In addition, the C-5 O-methyltransferase activity was measured in MA6233 with pAT1 and compared to MA6233 containing the pIJ922 vector and an OMT+ *S. avermitilis* strain containing pIJ922. MA6233 has less than 5% of the C-5 O-methyltransferase activity of the OMT+ strain, but MA6233 containing pAT1 had over 80% of the C-5 O-methyltransferase activity of the OMT+ strain. This conclusively demonstrates that pAT1 contains DNA which complemented the mutation in the OMT− strains tested and presumably encodes the gene for C-5 O-methyltransferase.

| Medium E | |
|---|---|
| MgSO$_4$.7H$_2$O (12.5% solution) | 4 ml |
| NaCl (12.5% solution) | 4 ml |
| MnSO$_4$.H$_2$O (0.5% solution) | 1 ml |
| ZnSO$_4$.7H$_2$O (1.0% solution) | 1 ml |
| CaCl$_2$.2H$_2$O (2.0% solution) | 1 ml |
| FeSO$_4$.7H$_2$O | 25 mg |
| KNO$_3$ | 2 g |
| Hy-Case SF (Humpko) | 20 g |
| Yeast Extract (Difco) | 20 g |
| Glucose | 20 g |
| Tween 80 | 100 mg |
| Distilled water, add to a final volume of | 1000 ml |
| Adjust pH to 7.0 with NaOH | |
| Medium F | |
| Peptonized Milk | 20 g |
| Ardamine pH | 4 g |
| Glucose | 90 g |
| MgSO$_4$.7H$_2$O | 0.5 g |
| CuSO$_4$.5H$_2$O | 0.06 mg |
| ZnSO$_4$6$_2$O | 1 mg |
| CoCl$_2$.6H$_2$O | 0.1 mg |
| FeCl$_2$.6H$_2$O | 3 mg |
| Agar | 15 g |
| Distilled water, add to a final volume of | 1000 ml |

Adjust to pH 7.2 with NaOH. After autoclaving add 4 ml of filter sterilized cyclohexamide solution (2.5 mg/ml) and 0.5 ml of thiostrepton solution (10 mg/ml in dimethyl formamide).

C. Characterization of pAT1.

pAT1 has a insert of about 20 kb, and a restriction map was determined for pAT1 which is indicated in FIG. 1 and Table 3. pAT1 was introduced into 5 other OMT− mutants and all were then able to make substantial amounts of avermectins with the O-methoxy at C-5. The location of the avrA gene was determined to reside on the 3.4 kb BamHI fragment located between 11.13 kb and 14.53 kb of the restriction map of pAT1. This was determined by subcloning the 3.4 kb fragment into the BamHI site of pIJ922 to construct pAT83. When pAT83 was introduced into MA6233, it also allowed the synthesis of avermectins A1a+b, A2a+b, B1a+b, and B2a+b.

TABLE 3

| Site # | Site Name | Interval (bp) | Co-ordinate (bp) |
|---|---|---|---|
| 1 | EcoR I | 1 | 1 |
| 2 | BamH I | 590 | 590 |
| 3 | Bgl II | 120 | 710 |
| 4 | Xho I | 810 | 1520 |
| 5 | EcoR V | 80 | 1600 |
| 6 | Sph I | 150 | 1750 |
| 7 | Sst I | 460 | 2210 |
| 8 | Sca I | 130 | 2340 |
| 9 | Bgl II | 350 | 2690 |
| 10 | BamH I | 400 | 3090 |
| 11 | Sca I | 470 | 3560 |
| 12 | BamH I | 230 | 3790 |
| 13 | Xho I | 1510 | 5300 |
| 14 | Xho I | 650 | 5950 |
| 15 | BamH I | 280 | 6230 |
| 16 | BamH I | 4900 | 11130 |
| 17 | Pst I | 1740 | 12870 |
| 18 | Sph I | 580 | 13450 |
| 19 | Sst I | 1030 | 14480 |
| 20 | BamH I | 50 | 14530 |
| 21 | Pst I | 100 | 14630 |
| 22 | BamH I | 2000 | 16630 |
| 23 | BamH I | 550 | 17180 |
| 24 | Xho I | 200 | 17380 |
| 25 | Sst I | 500 | 17880 |
| 26 | Xho I | 950 | 18830 |
| 27 | Sst I | 750 | 19580 |
| 28 | Pst I | 100 | 19680 |
| 29 | EcoR I | 300 | 19980 |
| 30 | Bgl II | 1000 | 20980 |
| 31 | Xba I | 4030 | 25010 |
| 32 | Sph I | 470 | 25480 |
| 33 | Sst I | 160 | 25640 |
| 34 | Nde I | 930 | 26570 |
| 35 | EcoR V | 505 | 27075 |
| 36 | Bgl II | 1375 | 28450 |
| 37 | Pst I | 910 | 29360 |
| 38 | Sca I | 980 | 30340 |
| 39 | Sph I | 210 | 30550 |
| 40 | Sph I | 370 | 30920 |
| 41 | Sst I | 1670 | 32590 |
| 42 | Sca I | 770 | 33360 |
| 43 | Sph I | 2380 | 35740 |
| 44 | Sph I | 6710 | 42450 |
| 45 | Xho I | 970 | 43420 |
| 46 | EcoR I | 630 | 44050 |

EXAMPLE 3

Isolation and characterization of pVE650

Plasmid pVE650 was isolated from the pIJ922-library. Protoplasts were prepared from S. avermitilis mutant MA6278 (AGL−, OMT−). 200 μl of protoplasts were transformed with 5μl of TE containing about 25 ng of the library DNA. The transformation mixture was diluted and plated on RM14 regeneration medium. After 20 hours incubation at 27° C., the plates were overlayed with 3 ml of RM14 containing 165μg/ml of thiostrepton and the incubation continued for 11 days. The transformation plates were placed at 4° C. and later, single colonies were picked with a sterile toothpick on to sporulation Medium D. After a further 5-7 days of incubation at 27°-28° C., sporulation was evident. Next, a 0.25 inch filter disk (Schleicher & Schuell, analytical paper #740-E) was wetted with growth Medium E, rubbed across the sporulated patch and used to inoculate production Medium F. After 12-16 days incubation at 27°-28° C., the mycelia was extracted with methanol, aliquots of the extract were applied to E. Merck Silica Gel 60 F-254 TLC plates and the avermectins developed for 14 minutes with a dichloromethane:ethylacetate:methanol 9:9:1 solvent mixture. Under these conditions MA6278 produces four spots representing avermectin aglycones. The order, from fastest to slowest band is, avermectin aglycone A1a+b, A2a+b, B1a+b, and B2a+b. (Although MA6278 is OMT− it retains low C-5 O-methyltransferase activity and this methylase apparently methylates the avermectin aglycones A1a+b and A2a+b more efficiently than the glycosylated avermectin). Over 3000 transformants were screened for production of glycosylated avermectins. An isolate which contained pVE650 was found to produce two spots which co-chromatographed with avermectins B1a+b and B2a+b. Plasmid DNA was isolated from this isolate and used to transform MA6278 and 25 other *S. avermitilis* mutants defective in synthesizing or attaching oleandrose to avermectin aglycone. Twenty-one regained the ability to produce avermectins containing oleandrose.

Figure 2:
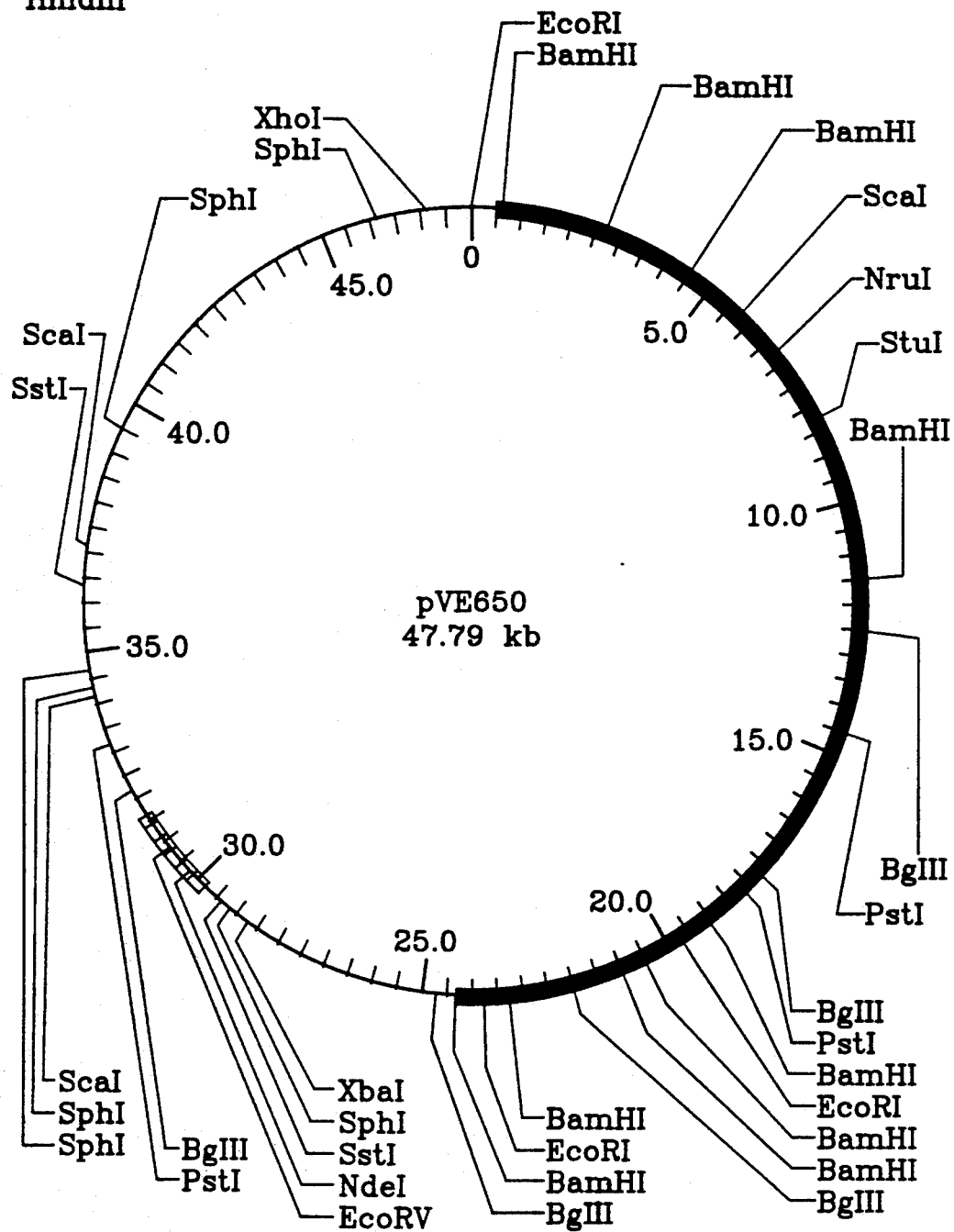
FIG. 2. Restriction map of pVE650. Only the sites mapped in both the vector and insert DNA are indicated.

A restriction map of pVE650 was determined and is indicated in Table 4 and FIG. 2. The location of genes for synthesis or addition of oleandrose to avermectin aglycones was determined by subcloning fragments from pVE650 into pIJ922 and introducing the resulting subclones into aglycone producing mutants. Three complementation classes, representing at least three genes, were discovered and are indicated in Table 2.

TABLE 4

Restriction sites in pVE650.

| Site # | Site Name | Interval (bp) | Co-ordinate (bp) |
|---|---|---|---|
| 1 | EcoR I | 1 | 1 |
| 2 | BamH I | 590 | 590 |
| 3 | BamH I | 2090 | 2680 |
| 4 | BamH I | 1820 | 4500 |
| 5 | Sca I | 1250 | 5750 |
| 6 | Nru I | 1000 | 6750 |
| 7 | Stu I | 1500 | 8250 |
| 8 | BamH I | 3250 | 11500 |
| 9 | Pst I | 1000 | 12500 |
| 10 | BamH I | 2000 | 14500 |
| 11 | Bgl II | 3250 | 17750 |
| 12 | Pst I | 350 | 18100 |
| 13 | BamH I | 1000 | 19100 |
| 14 | EcoR I | 570 | 19670 |
| 15 | BamH I | 810 | 20480 |
| 16 | BamH I | 20 | 20500 |
| 17 | BamH I | 530 | 21030 |
| 18 | Bgl II | 1000 | 22030 |
| 19 | Bgl II | 140 | 22170 |
| 20 | BamH I | 1080 | 23250 |
| 21 | EcoR I | 470 | 23720 |
| 22 | BamH I | 620 | 24340 |
| 23 | Bgl II | 390 | 24730 |
| 24 | Xba I | 4030 | 28760 |
| 25 | Nde I | 1560 | 30320 |
| 26 | EcoR V | 505 | 30825 |
| 27 | Bgl II | 1375 | 32200 |
| 28 | Pst I | 910 | 33110 |
| 29 | Sca I | 980 | 34090 |
| 30 | Sca I | 3020 | 37110 |
| 31 | EcoR I | 630 | 47800 |

EXAMPLE 4

A cloned avermectin gene alters the fermentation product composition: the cloned avermectin O-methyltransferase gene.

The presence of the cloned avermectin O-methyltransferase (OMT) gene on a plasmid in an avermectin producing strain alters the composition of the avemectins produced. *S. avermitilis* strains containing the wild type (unaltered) chromosomal OMT gene produce approximately 31% of the avermectins as the A components with a methoxyl group at C-5 and approximately 69% of the avermectins as the B components with a hydroxyl group at C-5. The mutant strain, MA6233, deficient in avermectin O-methyltransferase, produces only 4% of the avermectins as the A components and 96% of the avermectins as the B components. When plasmid pAT1, which contains the OMT gene, is transformed into the mutant strain MA6233, the avermectin composition is restored almost to the wild type strain levels with 26% of the avermectins as the A components and 74% of the avermectins as the B components.

When pAT1 is transformed into a strain with a functional wild type OMT gene, the levels of the avermectin A components is significantly increased to 66% while the proportion of the avermectin B components is lowered to 34%. These experiments provide an example of how the presence of a cloned gene in an avermectin producing strain can alter the fermentation product composition resulting in an efficient process to produce avermectin A1 and A2.

pAT1, when transformed into other Streptomyces strains that produce secondary metabolites, can alter these fermentations in a similar manner to the first example and result in the production of methylated derivatives of the natural fermentation product. These new and novel derivatives may be more potent and have improved activity spectra.

EXAMPLE 5

Isolation of other genes for avermectin biosynthesis

Ikeda et al have demonstrated that the genes for the synthesis of the avermectin aglycone are genetically linked to the genes for synthesis or attachment of the oleandrose moiety to avermectin aglycone. Thus, the other genes for avermectin biosynthesis can be cloned by isolating DNA adjacent to the insert DNA of pAT1 and pVE650 clones.

DNA adjacent to the insert in pVE650 was isolated from a cosmid library of *S. avermitilis* DNA. The cosmid vector used was pVE328, a cosmid vector which can replicate in *E. coli* conferring ampicilin-resistance (Amp$^r$) and Streptomyces conferring Thio$^r$. pVE328 is only 7.5 kb in size so it can clone DNA fragments up to 43 kb, and pVE328 contains two lambda cos sites so it can be efficiently packaged into phage heads in vitro. pVE328 also contains unique BglII and HpaI cloning sites flanked by DraI sites. The BglII cloning site allows the incorporation of fragments with GATC ends, which are produced by BamHI, BglII, BclI, XhoII, and MboI. The HpaI site can be used to clone blunt ended fragments. Since Streptomyces DNA has a high G+C ratio, often greater than 70%, the DraI site TTTAAA is very rare (1 per 300 kb). Thus, most fragments cloned into the BglII or HpaI sites can be excised with DraI for further analysis and manipulation. Finally the vector contains the broad host range Streptomyces phage TG1 cos site. This site can be used in vivo by TG1 helper phage to package pVE328 derivatives into TG1 virions. A TG1 lysate grown on a pVE328 derivative can then be used to introduce the pVE328 derivatives into other Streptomyces by phage mediated transduction. This technique is technically simpler than transformation and expands the hosts into which the clone may be introduced.

pVE328 was constructed using standard recombinant DNA technology differing little from the procedures in Maniatis et al., supra.

The starting plasmid was pSVO10X2 obtained from Rick Myers via F. Foor. pSVO10X2 is a deletion derivative of pBR322 which contains two multiple cloning regions and some SV40 DNA. A derivative of pSVO10X2 which contained a single multiple cloning region and lacked the SV40 DNA was isolated after a complex ligation. This ligation involved two digestions of pSVO10X2 (one with PstI, HindIII and PvuI and the other with BamHI, HindIII and PvuI), and the digestion of pMC1403 (obtained from M. Casadaban, University of Chicago), with BamHI, PstI, and PvuII. Among the products of this ligation was a 2 kb plasmid, designated pVE61, that was found to have a multiple cloning region containing sites for the enzymes EcoRI, SmaI, BamHI, PstI, BglII, XbaI, and HindIII. This plasmid was converted to an *E. coli* lambda cosmid by addition of 405 bp HincII cos fragment from pVE81, into the unique SmaI site of pVE61 to yield pVE105. The cos region in pVE81 had been previously cloned as a 3.2 kb EcoRI-BglII fragment from lambda into the EcoRI-BamHI sites of pBR322 to yield pVE81. The PstI site in the amp gene of pVE105 was removed by substituting the BglI to AatII fragment of pUC8 (Bethesda Research Laboratories, Gaithersburg, Md.) for the BglI to AatII fragment of pVE105 to yield pVE163. This cosmid was made into a shuttle cosmid by ligation of the Streptomyces plasmid pVE95 to pVE167. pVE95 is a stable, Thio$^r$ deletion derivative of pVE28 isolated after digestion of pVE28 with SstI and subsequent ligation. pVE95 was linearized at its unique BglII site and ligated to pVE163 linearized at its unique BamHI site to yield pVE167. Unique cloning sites were introduced into pVE167, linearized at its BglII site by the ligation of a synthetic oligonucleotide of sequence:

```
5' GATCGTTTAAAGTTAACAGATCTTTAAAG 3'
3'     CAAATTTCAATTGTCTAGAAATTTCCTAG 5'
```

Figure 4:
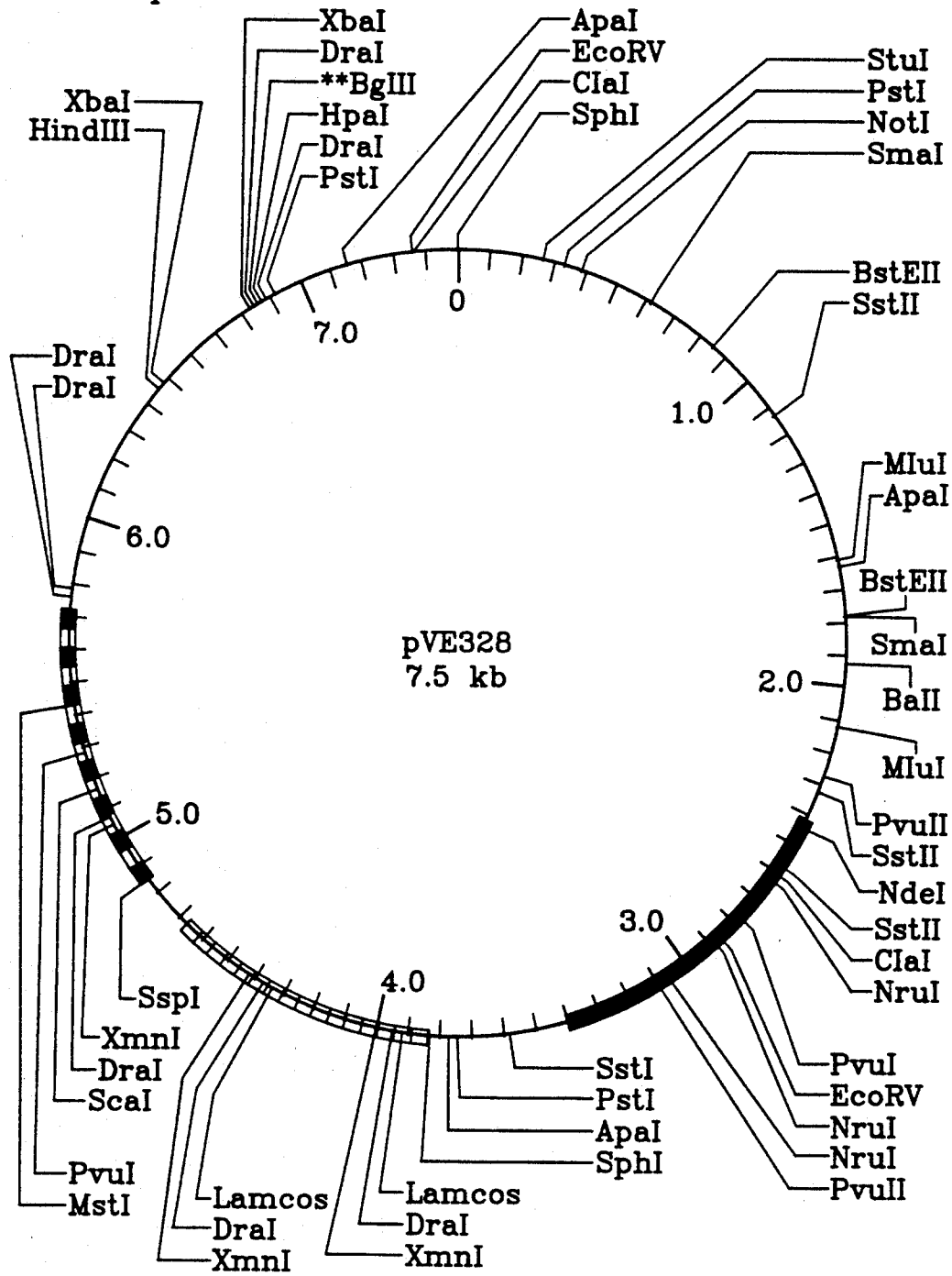
FIG. 4. Restriction map of pVE328.
Figure 5:
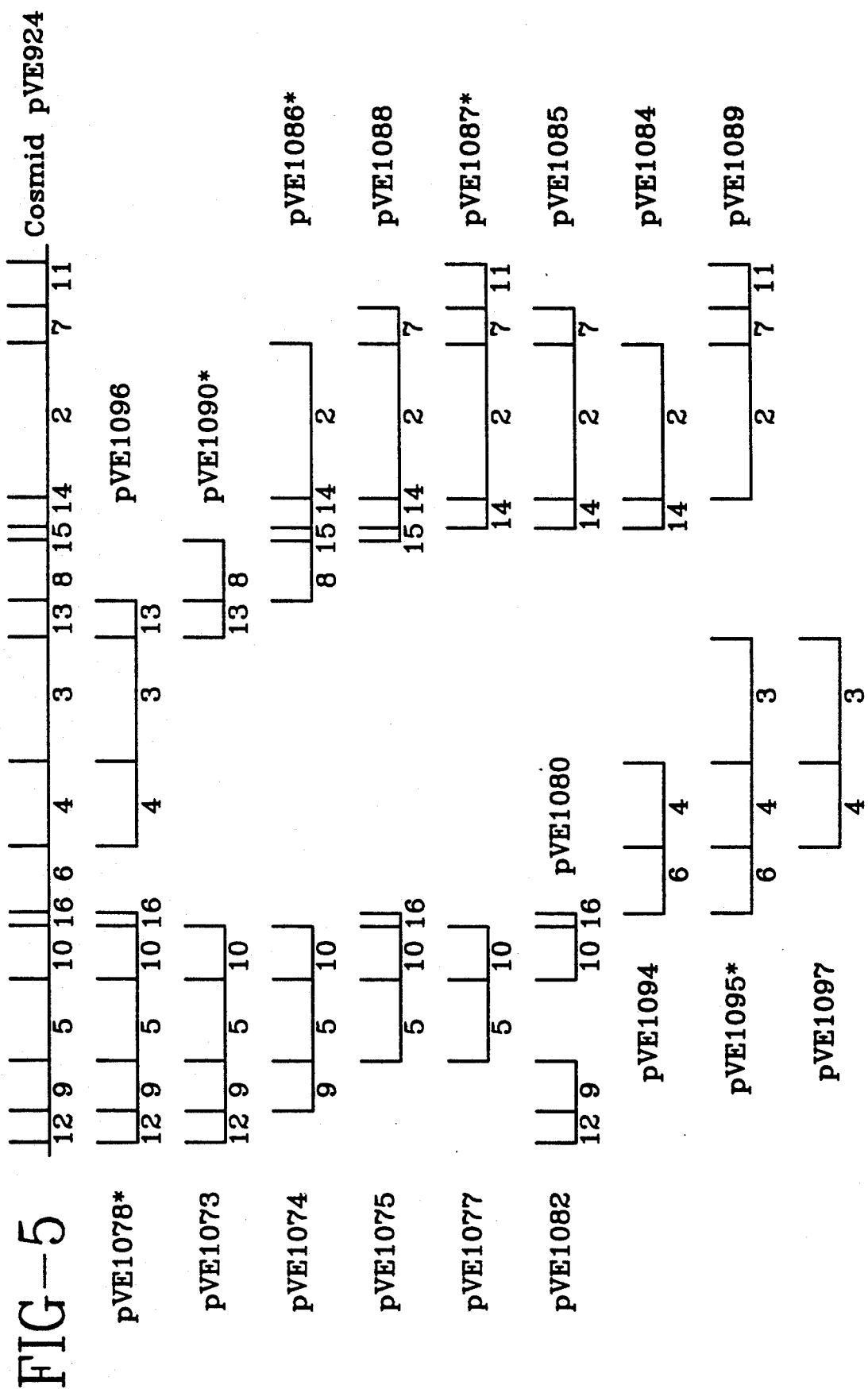
FIG. 5. Restriction map of the insert in cosmid pVE924 and BamHI partial subclones. Vertical lines represent BamHI sites. Numbers 2 to 15 represent the second largest fragment to the smallest BamHI fragments of pVE924 listed in Table 5. Plasmids indicated with an * were used in complementation tests.
Figure 6:
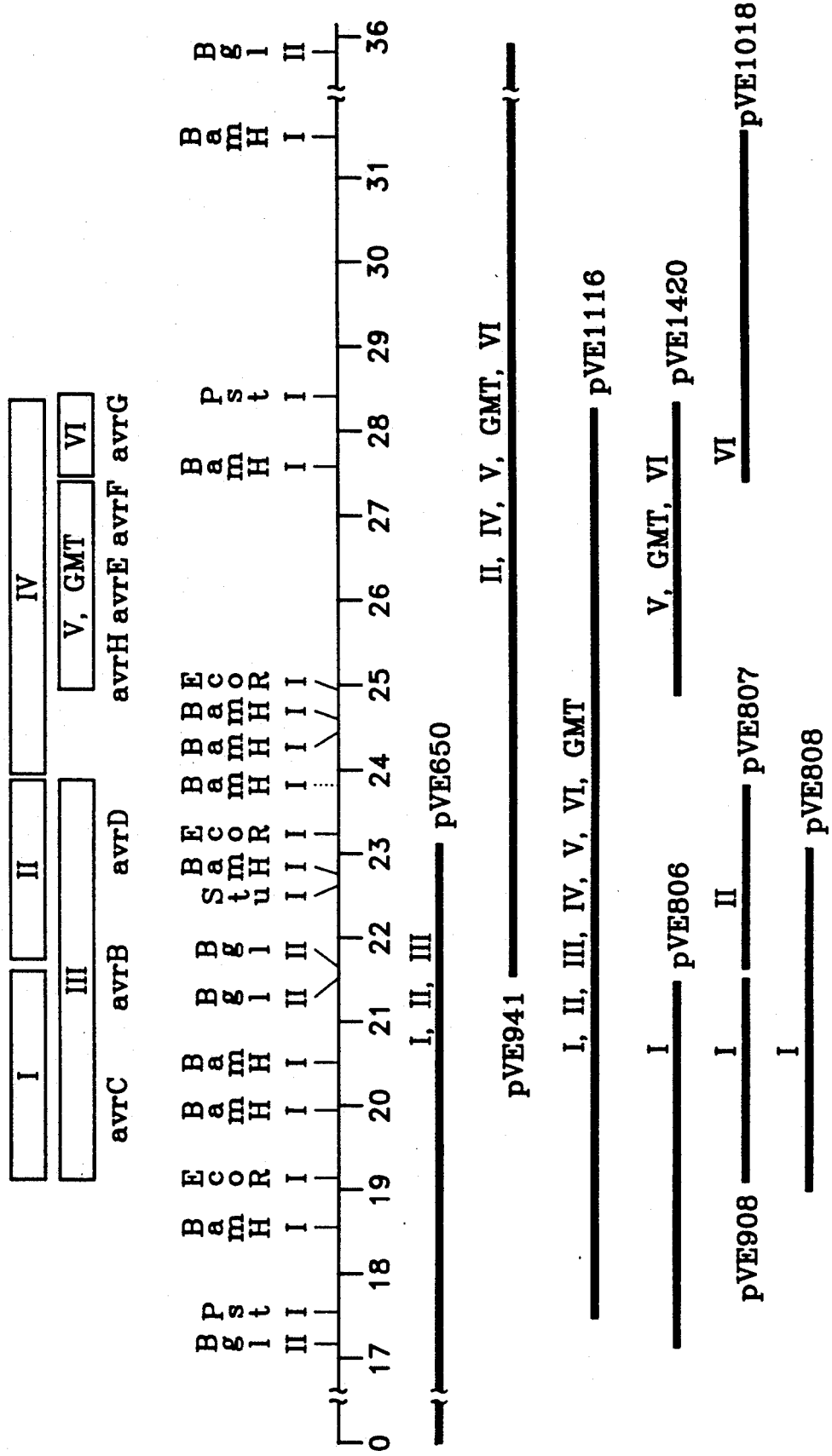
FIG. 6. A restriction map of the glycosylation region. The BamHI site indicated by a dotted line is present on pVE650 at the insert/vector junction but not in the chromosome. The zero kb origin represents the beginning of the insert in pVE650. The extent of DNA on pVE650, pVE1116, pVE941, pVE908, pVE806, pVE807, pVE808, pVE1018, and pVE1420 is indicated. The locations of regions which complement mutants defective in glycosylation of avermectin are indicated.

The double strand oligonucleotide was prepared by mixing together 10 μg of each single stranded 29 mer in 50 μl of TE, the mixture was heated to 85° C. for 5 minutes, slowly cooled to room temperature and stored overnight at 4° C. One half microgram of pVE167 was mixed with a 50 fold molar excess of annealed oligonucleotide and ligated with T4 DNA ligase. Among the Amp$^r$ transformants, an isolate containing a single copy of the oligonucleotide was identified and designated pVE232. pVE232 was converted into a Streptomyces phage TG1 cosmid by addition of a 270 bp EcoRV-HpaI fragment containing the TG1 cos site. pVE232 was linearized at its XbaI site, the site made blunt by treatment with DNA polymerase Klenow fragment (Bethesda Research Laboratories, Gaithersburg, Md.), and ligated to TG1 cleaved with HpaI and EcoRV. pVE288 was identified as derivative which contained the 270 bp cos fragment. The TG1 cos fragment can be cleaved from pVE288 with XbaI since insertion of the HpaI-EcoRV fragment into the filled in XbaI site regenerated two XbaI sites. A second lambda cos site was inserted into a pVE288 after it was digested with EcoRI and treated with DNA polymerase Klenow fragment. The resulting blunt-ended linear molecule of pVE288 was ligated to pVE81 digested with HincII and a derivative with two lambda cos sites in the same orientation was identified and designated pVE328. The primary cloning site, BglII, is indicated by ** in FIG. 4.

A library of *S. avermitilis* DNA was prepared in the cosmid vector pVE328. Partially digested Sau3A treated *S. avermitilis* chromosomal DNA was separated on a 15–40% sucrose gradient. Fractions containing fragments from 35 to 45 kb were pooled, the sucrose was removed by dialysis against TE buffer, and the fragments were concentrated by ethanol precipitation. About three micrograms of fragments were mixed with 0.5 or 0.2 μg of pVE328 in a total volume of 20 μl. The pVE328 DNA had been previously cleaved at its single BglII site and treated with CIAP. After ligation at 12° C. for 16 hours with T4 DNA ligase, 4 μl of the DNA mixture was packaged into phages with an Ambersham lambda in vitro packaging kit. The cosmid library was transduced into *E. coli* strain RR1 selecting Amp$^r$. 2016 transductants were picked individually into cells of microtiter dishes containing 0.15 ml of LB medium with 75 μg/ml of ampicillin, grown overnight at 37° C., 15 μl of dimethyl sulfoxide was added, the plates were sealed in Seal-A-Meal bags and quick frozen in a dry ice/ethanol bath and stored at −80° C. This was the cosmid library of *S. avermitilis*.

Filters containing DNA from the cosmid library were prepared by growing a replica of the library on LBamp agar (75 μg/ml of ampicillin). Before cultures of the 2016 clones were frozen, 5 μl aliquots from each culture were transferred to LB amp agar (75 μg/ml of ampicillin) in an 8 by 12 pattern. After overnight incubation at 37° C., an ICN Biotrans nylon membrane (1.2 micron rating) was placed on the colonies for 1 hour and incubation continued at 37° C., then the filters were transferred, colony side up, to LB-amp agar for 4 hours of further incubation at 37° C. The filters were then transferred to LB-amp-cam agar (50 μg/ml chloramphenicol) and incubated overnight at 37° C. DNA was released from the cells and fixed to the filters by transferring the filters to a series of Whatmann 3 MM filters saturated with various solutions. Between each transfer the filters were placed on dry 3 MM paper to blot off excess solutions. The filters were transferred to 3 MM saturated with 10% SDS for 5 minutes at room temperature, then the cells were lysed by transferring the filters to 3 MM saturated with 0.5 N NaOH, 1.5 N NaCl for 5 minutes at room temperature and then placed in a 100° C. steam cabinet for an additional 5 minutes. The filters were neutralized by transfer to 3 MM saturated with 0.5M Tris, pH 7.9, 1.5N NaCl and incubated at room temperature for 5 minutes. The filters were then immersed in a solution of 2×SSC (SSC is 0.15M NaCl, 0.015M trisodium citrate, pH 7.0) for 2 seconds, then immersed in 95% ethanol for 10 seconds, air dried, and baked at 80° C. for 1 hour in a vacuum oven. The residual cell debris was removed by three washings of the filters at 65° C. in 0.1% SDS, 3×SSC, each wash for 15 minutes. After washing, the filters were dipped in 2×SSC, air dryed on 3 MM paper and saved at 4° C. until used.

Twenty-one filters each containing DNA from 96 cosmid clones was probed using the 1.09 kb BamHI fragment from one end of plasmid pVE650. This DNA was labelled with 32-P dCTP using a random priming kit (U.S. Biochemicals, Cleavland, Ohio). The purified 1.09 kb BamHI fragment (0.5 μg) in 5 μl of TE was denatured by heating at 95° C. for 10 minutes and then chilling on ice for 10 minutes. The following were added to the DNA: 3 μl of a 1:1:1 mixture of dATP:dTTP:dGTP, 2 μl of 10×reaction mixture containing the random hexanucleotides, 3 μl of H$_2$O, 5 μl of [$^{32}$P] dCTP (specific activity of 3000 Ci/mmole), and 1 μl of klenow enzyme. The mixture was mixed, microfuged for 10 seconds, then incubated for 30 minutes at 37° C. The reaction was terminated by adding 2 μl of 0.25M EDTA, pH 8. The labelled 1.09 kb fragment was passed through a Centri-Sep Column (Princeton Seperations, Adelphia, N.J.)by centrifugation at 12,000 rpm for 3 minutes at 4° C. Each of the 21 filters was put into a separate plastic Seal-A-Meal bag #6006 (Dazey Corp., Industrial Airport, Kans.), 9.5 ml of prehybridization solution was added, and the bag heat sealed. Prehybridization solution contained 0.75M NaCl, 0.075m NaCitrate, pH 7.0, 0.1% Ficoll, 0.1% polyvinylpyrrolidone, 0.1% BSA, 50% formamide, 0.1% SDS, and 100 μg/ml of sheared herring sperm DNA that was heat denatured for 10 minutes in a boiling water bath. After a 3 hour incubation at 43° C., the prehybridization solution was removed and 12 ml of a hybridization solution was added to the same bag containing each of the 21 filters. The hybridization solution was modified prehybridization solution that contained 10% dextran sulfate.

The probe was heated at 95° C. for 10 minutes then put on ice. A total of $2 \times 10^6$ counts was added to each hybridization bag and the bags were heat sealed. After sealing an effort was made to distribute the probe evenly throughout the hybridization solution. The hybridization was carried out at 43° C. overnight in a water bath with slow agitation. After 18 hours the filters were removed from the bags and rinsed two times in 0.3M NaCl, 0.03M NaCitrate, pH 7.0, 1% SDS at room temperature. The filters were then washed twice in 0.3M NaCl, 0.03M sodium citrate, pH 7.0, 0.1% SDS for 15 minutes at 43° C. The filters were then washed twice in 0.015M NaCl, 0.0015M sodium citrate, pH 7.0, 0.1% SDS for 10 minutes at 43° C., and twice in 0.015M NaCl, 0.0015M sodium citrate, pH 7.0, 0.1% SDS for 10 minutes at 60° C. All the filters were blotted on Whatman 3 MM paper and exposed to X-ray film (Kodak X-OMAT AR-5) for 14 days. This initial screen yielded 81 putative clones.

The individual cosmid cultures that yielded a positive signal to the 1.09 kb BamHI fragment were spotted in triplicate on LB plates containing 100 μg/ml of ampicillin and incubated overnight at 37° C., refrigerated for 2 hours at 4° C., a 82 mm nitrocellulose filter (Schleicher and Schuell, BA85, 0.45 micron) placed on the plates for 2 minutes, and then the filter containing bacteria was placed on LB agar plates containing 10 μg/ml of chloramphenicol with the colony side up. The plates were incubated for 12 hours at 37° C. and then the bacteria were lysed and the DNA fixed to the filters. The bacterial colonies on the filters were lysed by laying the filters, colony side up, on a sheet of Whatman 3 MM paper soaked with 0.5M NaOH for 3 minutes. Next the filters were moved to another sheet of Whatman 3 MM paper containing 0.5M NaOH and left for an additional 3 minutes. The filters were then transferred to Whatman 3 MM paper containing neutralization buffer (1.0M TrisHCl pH8/1.5M NaCl) for 3 minutes. The above step was repeated. The filters were removed and placed on Whatman 3 MM paper and allowed to air dry for 30 minutes. The dried filters were sandwiched between two sheets of 3 MM paper and baked for 45 minutes at 80° C. in a vacuum oven. The baked filters were then hybridized with 32-P labelled 1.09 kb BamHI fragment as described above. Of the 81 initial putative clones, 9 colonies gave a positive signal on all three filters. The nine cosmid clones were grown in liquid culture to isolate large amounts of purified DNA for restriction analysis.

The 21 filters containing the cosmid libary described above were stripped of the hybridized probe and probed with the 2.09 kb BamH I fragment from the other end of pVE650. The filters, which were not allowed to dry, were stripped of the probe by washing 2 times for 20 minutes in 500 ml of 0.015M NaCl, 0.0015M NaCitrate, pH 7.0, 0.5% SDS at 95° C. The filters were exposed to X-Ray film for 48 hours to insure that the probe was removed. The 21 filters were then probed as described above for the 1.09 kb fragment except the probe was the 2.09 kb BamHI fragment. The initial screen of the library yielded 93 putative cosmids that hybridized with the 2.09 kb BamHI fragment from pVE650. Upon retest, 12 of the cosmids were positive and DNA was purified from the 12 clones.

Figure 3:
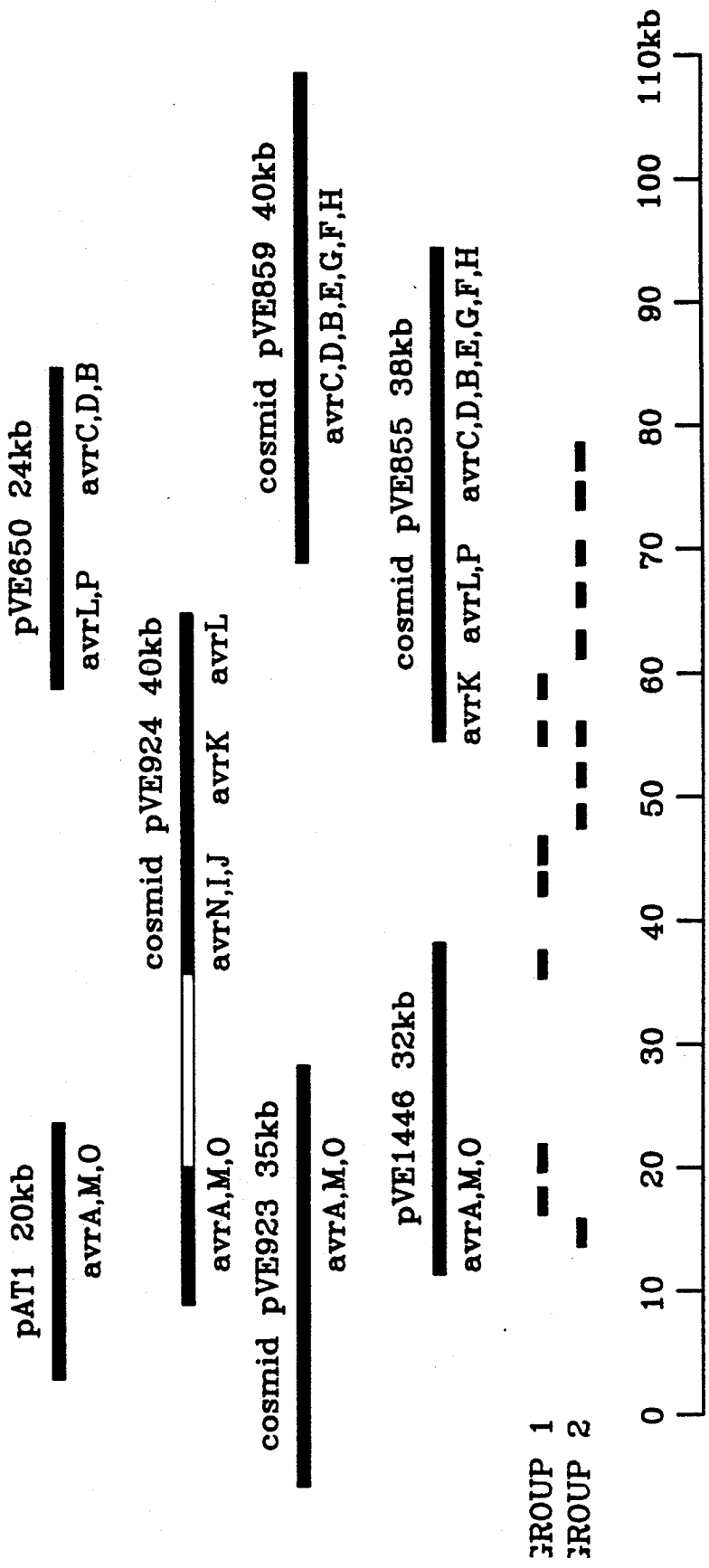
FIG. 3. A map of the avermectin gene cluster. The extent of DNA contained on pVE923, pAT1, pVE1446, pVE924, pVE855, pVE650, pVE1116, and pVE859 is indicated. The deleted region on pVE924 is indicated by a hollow line. Regions which complement avermectin mutants are indicated. avrA is the gene for avermectin C-5 O-methyltransferase. avrB, C, D, E, G, and H represent genes defective in the Class III, Class I, Class II, Class IV, Class VI, and Class V, aglycone producing mutants. avrF is the gene for avermectin glycosyl O-methyltransferase. Avermectin C-22, C-23 dehydrase is designated avrI, the gene involved in forming the furan ring in avermectin is designated avrJ, and six genes involved informing the macrocyclic lactone ring are designated avrK, avrL, avrM, avrN, avrO and avrP. The approximate locations of regions of related sequences in Group 1 and Group 2 are indicated.

The various cosmid clones were mapped by restriction analysis relative to the BamHI fragments in pAT1 and pVE650. In addition a Southern analysis was performed to identify which clones contained fragments from the Group 1 and Group 2 homology groups. This allowed the identification of 4 clones which collectively represent over 110 kb of genomic DNA. Their location relative to pAT1 and pVE650 is indicated in FIG. 3. To test if these clones contain DNA for other avermectin genes, fragments were subcloned from the cosmids onto pIJ922. One subclone, pVE941, contained a 14 kb BglII fragment from pVE859. This DNA was transformed into aglycone producing mutants that were not complemented by pVE650. All five mutants regained the ability to produce glycosylated avermectins. In addition, this DNA was introduced into MA6316 (GMT−), and MA6323 (GMT− OMT−) mutants which do not methylate the 3' and 3" hydroxyls of avermectin. These mutants were also complemented (Class GMT in Table 2).

The genes for glycosylation on pVE650 and pVE941 can be subcloned onto a single plasmid. A restriction digestion of pVE859 with PstI produced 8 bands. The largest PstI fragment was gel purified and cloned into pVE1043 to form pVE1116. (pVE1043 was derived from pIJ922 in two steps. First, pVE1023 was made by destroying the PstI site in pIJ922 by cleaving pIJ922 with PstI and filling in that site using T4 DNA polymerase. pVE1043 was constructed by inserting a synthetic oligonucleotide into pVE1023 digested with EcoRI and BamHI. The oligonucleotide consisted of the sequence:

```
5' AATTCGTTAACTGCAGCTAGCATTAATAAGCTTTAAAG 3'
3' GCAATTGACGTCGATCGTAATTATTCGAAATTTCCTAG 5'
```

This resulted in the formation of a polycloning site with unique sites for EcoRI, HpaI, PstI, NheI, AseI, HindIII, DraI, and BamHI.) pVE1116 complemented all Class III, Class IV, Class V, Class VI and GMT mutants. In addition it was confirmed to complement a representative mutant from Class I and Class II. Thus, it appears that pVE1116 contains all the genes for glycoyslation of avermection. This plasmid will allow the biotransformation of avermectin aglycones into avermectin. When this plasmid is introduced into other strains producing antibiotics which contain an appropriate free hydroxyl, this plasmid will add oleandrose to the antibiotics to make novel antibiotics. These novel antibiotics may have enhanced activity.

A comparison of the restriction maps of pAT1, pVE923 and pVE924 showed that the region adjacent to the 0.55 kb BamHI fragment was different in the three clones. On pAT1, a 3.4 kb BamHI to vector junction fragment, which contains an EcoRI site, maps adjacent to the 0.55 kb BamHI fragment. On pVE924 a 3.2 kb BamHI fragment without an EcoRI site is located adjacent to the 0.55 kb BamHI fragment. Cosmid pVE923 has a 7.0 kb BamHI fragment located adjacent to the 0.55 kb BamHI fragment. In order to determine the actual structure of this region of the avermectin gene cluster, DNA form the S. avermitilis chromosome was directly cloned into E. coli.

The method chosen to directly clone DNA from S. avermitilis into E. coli relies on the homologous recombination system of S. avermitilis to direct the integration of an E. coli plasmid. The E. coli plasmid contains two fragments of the avemectin cluster which flank a region of interest. Such a plasmid will integrate by recombination between the genome and one of the homologous fragments. The resulting integrant has a duplication of each region represented by the two cloned fragments. Recombination between the duplicated regions will result in excision of the vector. If this recombination occurs between a different region than the recombination which resulted in integration, then the resulting excision plasmid will contain the two cloned fragments and all the DNA between them.

Any E. coli vector which does not replicate in Streptomyces can be used if it has the following features: a gene foe selection in E. coli, a gene for selection in Streptomyces, and unique sites for cloning two fragments. For these experiments a derivative of pVE616 was made. pVE616 already contained a gene for selection E. coli (amp) and a gene for selection in Streptomyces (thio). A synthetic oligonucleotide was made to provide useful cloning sites of the following sequence:

```
5' GATCCGACTGTTAACAGATCTGAGCTCTGCA 3'
3'     GCTGACAATTGTCTAGACTCGAG       5'
```

The oligonucleotide was cloned into the BamHI to PstI sites of pVE616 resulting in a pVE1011 with a polycloning site for BamHI, HpaI, BglII, SstI and PstI. FIG. 7 displays a restriction map of pVE1011. The two fragments chosen for cloning into pVE1011 flank the 0.55 kb BamHI fragment. The 3.4 kb BamHI fragment of pAT1 and the 3.7 kb BamHI fragment from pVE924 were chosen (see Table 6). The 3.4 kb BamHI fragment of pAT1 was purified from an agarose gel and ligated to BglII digested, CIAP treated pVE1011. After transformation of E. coli, Amp$^r$ transformants were screened for the insert. One transformant, contained a plasmid with a 3.4 kb insert and the plasmid was designated pVE1038. pVE1038 was isolated from 500 ml of LBamp (LB containing 100 μg/ml of ampicillin) grown culture and purified by CsCl banding. Next pVE1038 was digested with BamHI and HpaI and ligated to a gel purified, 2.9 kb BamHI-HpaI fragment of Tn5. The resulting Neo$^r$Amp$^r$ transformant contained a plasmid pVE1051, with the 2.9 kb fragment. pVE1051 was isolated from 500 ml of LBamp grown culture and purified by CsCl banding. Next pVE1051 was digested with BamHI, treated with CIAP, and ligated to the gel purified 3.7 kb BamHI fragment of pVE924. A transformant was identified with the 3.7 kb insert and the orientation of the 3.4 kb and 3.7 kb BamHI fragments were the same as in the chromosome. The DNA of the plasmid, designated pVE1299, was transformed into the DNA methylation deficient strain, MB5386. S. avermitilis has a methyl specific restriction system (J. Bact. 170 pg 5607–5612 (1988)). Thus, before DNA can be introduced into S. avermitilis from E. coli it must be isolated from a strain deficient in dam and dcm methylation. Five μg of CsCl purified DNA of pVE1299, isolated from MB5386, was introduced into 100 μl of S. avermitilis protoplasts. Transformants were selected as Neo$^r$ Thio$^r$ and one, designated GG1776, was saved. Small scale plasmid preparations were made from 6 ml of GG1776 grown in YEME with 5 μg/ml thiostrepton and with 5 μg/ml neomycin. Ten microliters of the resulting DNA preparation was used to transform E. coli and Amp$^r$Neo$^s$ transformants were examined. As expected, these transformants contained the 3.4 kb, 2.1 kb, 0.55 kb BamHI fragments, as well as the 7.0 kb BamHI band of pVE923. Surprisingly the transformants also contained two new BamHI fragments of 8.0 kb and 7.4 kb. The 7.0 kb, 8.0 kb, and 7.4 kb fragments are absent from pVE924 and pAT1. Thus pVE924 contained a deletion of DNA between the 0.55 kb and 3.7 kb BamHI bands resulting in the 3.2 kb BamHI fragment. One transformant, ET14167, with a plasmid designated pVE1446, was saved. Restriction mapping then established the order of fragments on pVE1446 (see Table 6). It is likely the DNA represented by the 7.4 kb and 8.0 kb BamHI fragments contains avermectin genes since avermectin genes have been located on either side of this region. The E. coli strain containing pVE1446 has been designated MB5472 and deposited as ATCC 68250.

TABLE 5

Size of BamHI fragments on plasmids containing S. avermitilis DNA in kilobase pairs.

| PVE923 | PAT1 | pVE1446 | pVE924 | pVE855 | pVE650 | pVE859 |
|---|---|---|---|---|---|---|
| 17.50 | 27.45 | 8.00 | 9.10 | 10.00 | 24.05 | 13.60 |
| 7.40 | 4.90 | 7.60 | 5.50 | 7.40 | 7.40 | 5.70 |
| 7.00 | 3.40 | 7.40 | 4.90 | 5.60 | 4.70 | 5.50 |
| 3.60 | 2.50 | 7.00 | 3.70 | 4.70 | 3.00 | 4.70 |
| 2.10 | 2.44 | 3.70 | 3.40 | 3.30 | 2.35 | 4.00 |
| 1.75 | 2.10 | 2.10 | 3.15 | 3.00 | 2.09 | 3.20 |
| 1.50 | 0.70 | 0.55 | 2.60 | 2.60 | 1.85 | 3.00 |
| 0.85 | 0.55 |  | 2.44 | 2.50 | 1.40 | 2.35 |
| 0.58 |  |  | 2.30 | 2.35 | 1.09 | 1.65 |
| 0.55 |  |  | 2.10 | 1.85 | 0.53 | 1.40 |
|  |  |  | 1.90 | 1.60 | 0.02 | 0.53 |
|  |  |  | 1.30 | 1.40 |  | 0.02 |
|  |  |  | 1.20 | 0.95 |  |  |
|  |  |  | 0.95 | 0.75 |  |  |
|  |  |  | 0.75 | 0.53 |  |  |
|  |  |  | 0.55 | 0.02 |  |  |

TABLE 6

Restriction map of the avermectin gene cluster.

| Site # | Site[1] Name | Interval (bp) | Co-ordinate (bp) |
|---|---|---|---|
| 1 | BamHI | 1300 | 1300 |
| 2 | BamHI | 2300 | 3600 |
| 3 | PstI | 1740 | 5340 |
| 4 | BamHI | 1660 | 7000 |
| 5 | PstI | 100 | 7100 |
| 6 | BamHI | 2000 | 9100 |
| 7 | BamHI | 550 | 9650 |
| 8 | EcoRI | 6800 | 16450 |
| 9 | BamHI | 200 | 16650 |
| 10 | StuI | 4300 | 20950 |
| 11 | BamHI | 3100 | 24050 |
| 12 | StuI | 7700 | 31750 |
| 13 | BamHI | 300 | 32050 |
| 14 | BamHI | 3700 | 35750 |
| 15 | BamHI | 4900 | 40650 |
| 16 | BamHI | 1200 | 41850 |
| 17 | BamHI | 2440 | 44290 |
| 18 | BamHI | 750 | 45040 |
| 19 | BamHI | 950 | 45990 |
| 20 | BamHI | 5500 | 51490 |
| 21 | BamHI | 2600 | 54090 |
| 22 | BamHI | 1900 | 55990 |
| 23 | ScaI | 100 | 57690 |
| 24 | StuI | 2300 | 59990 |
| 25 | ScaI | 1300 | 61290 |
| 26 | BamHI | 1700 | 62990 |
| 27 | PstI | 2000 | 64990 |
| 28 | BamHI | 1000 | 65990 |
| 29 | BglII | 3350 | 69340 |
| 30 | PstI | 350 | 69690 |
| 31 | BamHI | 1000 | 70690 |
| 32 | EcoRI | 570 | 71260 |
| 33 | BamHI | 830 | 72090 |
| 34 | BamHI | 20 | 72110 |
| 35 | BamHI | 530 | 72640 |
| 36 | BglII | 1130 | 73770 |
| 37 | BglII | 140 | 73910 |
| 38 | StuI | 980 | 74890 |
| 39 | BamHI | 100 | 74990 |
| 40 | EcoRI | 470 | 75460 |
| 41 | BamHI | 1180 | 76640 |
| 42 | BamHI | 200 | 76840 |
| 43 | EcoRI | 400 | 77240 |
| 44 | BamHI | 2800 | 80040 |
| 45 | PstI | 1290 | 81330 |
| 46 | BamHI | 2710 | 84040 |
| 47 | BglII | 3290 | 87330 |
| 48 | BamHI | 2410 | 89740 |
| 49 | BamHI | 5500 | 95240 |

[1]The BamHI sites in this 95 kb region have been mapped. Only some of the BglII, EcoRI, PstI, StuI, and ScaI sites have meen mapped.

What is claimed is:

1. Plasmid pAT1 (44.05 kb), pVE650, pVE923, pVE924, pVE855 and pVE859, and pVE1446.

2. The plasmid of claim 1 which is pAT1 (44.05 kb).

3. The plasmid of claim 1 which is pVE650.

4. The plasmid of claim 1 which is pVE923, pVE924, pVE855, or pVE859.

5. The plasmid pVE1446.

6. The DNA responsible for avermectin biosynthesis contained on plasmid pAT1 (44.05 kb), pVE650, pVE923, pVE924, pVE885, pVE859, or pVE1446.

7. A method for improving the yields of avermectin compounds from fermentation broths containing a microorganism capable of producing avermectin compounds which comprises incorporating one or more of the plasmids pAT1, (44.05 kb) pVE650, pVE923, pVE924, pVE855, pVE859, or pVE1446 or BamHi restriction fragments from said plasmids into such microorganism.

8. The method of claim 7 wherein the microorganism is Streptomyces.

9. The process of claim 8 wherein the microorganism is Streptomyces avermitilis.

10. The method of claim 8 wherein the microorganism is Streptomyces hygroscopicus.

11. The process of claim 8 wherein the microorganism is Streptomyces cyanogriseus.

12. The process of claim 8 wherein the microorganism is Streptomyces thermoarchaenosis.

13. The method of claim 7 wherein the plasmid is pAT1 (44.05 kb).

14. The method of claim 7 wherein the plasmid is pVE650.

15. The method of claim 7 where the plasmid is pVE923, pVE924, pVE855 or pVE859.

16. The method of claim 7 where the plasmid is pVE1446.

17. A process for the isolation of DNA from microorganisms comprising:
   a) constructing a cosmid library of DNA from a microorganism in *Escherichia coli*;
   b) preparing filters which contain DNA from said cosmid library;
   c) incorporating $^{32}$P into a purified Bam HI restriction DNA fragment comprising a portion of the DNA responsible for avermectin biosynthesis wherein said Bam HI fragment is contained on a plasmid selected from the group consisting of pAT1 (44.05 kb), pVE650, pVE923, pVE924, pVE855, pVE859, and pVE1446;
   d) using the $^{32}$P containing DNA of step c) as a probe in DNA—DNA hybridization with the filter from step b); and
   e) isolating the cosmid DNA from a replica of the colony which hybridized to the $^{32}$P containing DNA of step c).

18. A process of claim 17 wherein the microorganism is Streptomyces.

19. The process of claim 17 wherein DNA fragments are prepared from plasmids pAT1 (44.05 kb), pVE650, pVE923, pVE924, pVE855 or pVE859 or pVE1446.

20. The process of claim 17 wherein the Bam Hi restriction fragments are prepared from plasmid pAT1.

21. The process of claim 17 wherein the Bam Hi restriction fragments are prepared from plasmid pVE650.

22. The process of claim 17 wherein the Bam Hi restriction fragments are prepared from plasmids pVE923, pVE924, pVE855 or pVE859.

23. The process of claim 17 wherein the Bam Hi restriction fragments are prepared from plasmid pVE1446.

24. A process for the isolation of avermectin genes from *Streptomyces avermitilis* which comprises the complementation of *Streptomyces avermitilis* mutants with cloned *Streptomyces avermitilis* DNA wherein the cloned Streptomyces avermitilis DNA is contained on a plasmid selected from the group consisting of pVE650, pAT1 (44.05 kb), pVE923, pVE924, pVE855, pVE859, and pVE1446.

25. The process of claim 24 wherein the plasmid is pAT1 (44.05 kb).

26. The process of claim 24 wherein the plasmid is pVE650.

27. The process of claim 24 wherein the DNA is contained on plasmid pVE923, pVE924, pVE855 or pVE859.

28. The process of claim 24 wherein the DNA is contained on plasmid pVE1446.

29. The microbiological strain *Streptomyces lividans* containing plasmid pAT1 (44.05 kb).

30. A microbiological strain of claim 29 which is MA6619 (ATCC 67820) and mutants thereof.

31. The microbiological strain *Streptomyces lividans* containing plasmid pVE650.

32. A microbiological strain of claim 31 which is MA6618 (ATCC 67819) and mutants thereof.

33. A microbiological strain *Escherichia coli* containing plasmid pVE923.

34. A microbiological strain of claim 33 which is MB5373 (ATCC 67891) and mutants thereof.

35. The microbiological strain *Escherichia coli* containing plasmid pVE924.

36. The microbiological strain of claim 35 which is MB5374 (ATCC 67892) and mutants thereof.

37. The microbiological strain *Escherichia coli* containing plasmid pVE855.

38. The microbiological strain of claim 37 which is MB5370 (ATCC 67889) and mutants thereof.

39. A microbiological strain *Escherichia coli* containing the plasmid pVE859.

40. The microbiological strain of claim 39 which is MB5372 (ATCC 67890) and mutants thereof.

41. A microbiological strain *Escherichia coli* containing the plasmid pVE1446.

42. The microbiological strain of claim 41 which is MB5472 (ATCC 68250) and mutants thereof.

43. A Bam HI restriction fragment comprising a portion of the DNA responsible for avermectin biosynthesis wherein said Bam HI fragment is contained on pAT1 (44.05 kb).

44. A Bam HI restriction fragment comprising a portion of the DNA responsible for avermectin biosynthesis wherein said Bam HI fragment is contained on plasmid pVE650.

45. A Bam HI restriction fragment comprising a portion of the DNA responsible for avermectin biosynthesis wherein said Bam HI fragment is contained on a plasmid selected from the group consisting of pVE923, pVE924, pVE855, and pVE859.

46. A Bam HI restriction fragment comprising a portion of the DNA responsible for avermectin biosynthesis wherein said Bam HI fragment is contained on plasmid pVE1446.

* * * * *